United States Patent [19]

Nestor et al.

[11] Patent Number: 5,543,414
[45] Date of Patent: Aug. 6, 1996

[54] ACHIRAL AMINO ACID ACYL ESTERS OF GANCICLOVIR AND ITS DERIVATIVES

[75] Inventors: John J. Nestor, Cupertino; Scott W. Womble, Fremont; Hans Maag, Menlo Park, all of Calif.

[73] Assignee: Syntex (USA) Inc., Palo Alto, Calif.

[21] Appl. No.: 282,142

[22] Filed: Jul. 28, 1994

[51] Int. Cl.[6] ............ A61K 31/52; C07D 473/32; C07D 473/18
[52] U.S. Cl. ............ 514/262; 544/276; 544/277
[58] Field of Search ............ 514/262; 544/276, 544/277

[56] References Cited

U.S. PATENT DOCUMENTS

| | | | |
|---|---|---|---|
| 4,355,032 | 10/1982 | Verheyden et al. | 424/253 |
| 5,043,339 | 8/1991 | Beauchamp | 544/276 |

FOREIGN PATENT DOCUMENTS

| | | |
|---|---|---|
| 0158847 | 10/1985 | European Pat. Off. . |
| 0308065 | 3/1989 | European Pat. Off. . |
| 0375329 | 6/1990 | European Pat. Off. . |
| 1523865 | 9/1978 | United Kingdom . |
| 2104070 | 3/1983 | United Kingdom . |
| 2122618 | 1/1984 | United Kingdom . |
| WO94/29311 | 12/1994 | WIPO . |

OTHER PUBLICATIONS

E. Jensen et. al., *Acta Pharm. Nord.* 3(4) 243–247 (1991).
John C. Martin et. al., *J. Pharm. Sci.* 76(2), pp. 180–184 (1987).
P. C. Maudgal et. al., *Arch. Ophthalmol.* 1984; 102: 140–142.
Leon Colla et. al., *J. Med. Chem.* 98, 3, 26, 602–604 (1983).
L. M. Beauchamp et. al., *Antiviral Chemistry & Chemotherapy* (1992), 3 (3), 157–164.
Derwent for JP 05–097887 (Apr. 1993).

*Primary Examiner*—Mark L. Berch
*Attorney, Agent, or Firm*—Heller Ehrman White & McAuliffe

[57] ABSTRACT

Compounds of the Formula I

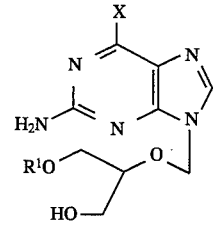

wherein X is hydrogen, chloro, amino or hydroxy; $R^1$ is an achiral amino acid acyl residue with a tertiary α-carbon atom. Preferred achiral amino acid acyl residues have the formula

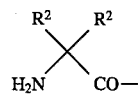

wherein each $R^2$ is alkyl with 1 to 6 carbon atoms, cycloalkyl with 3 to 5 carbon atoms, or benzyl; or the two $R^2$ groups link together to form a polymethylene group with 3 to 9 carbon atoms, and pharmaceutically acceptable salts thereof are antiviral agents with improved absorption. Intermediates for the preparation of the compounds of Formula I are also described.

25 Claims, No Drawings

ACHIRAL AMINO ACID ACYL ESTERS OF GANCICLOVIR AND ITS DERIVATIVES

BACKGROUND OF THE INVENTION

1. Field of the Invention

The present invention relates to novel antiviral drugs, particularly amine acid esters of purine derivatives, and most particularly to such esters derived from ganciclovir and an achiral amine acid characterized by a tertiary α-carbon atom and derivatives thereof. The invention also relates to intermediate compounds, synthetic methods for making the antiviral drugs, and to methods of antiviral and related disease treatment, and pharmaceutical compositions therefor.

2. Background Information

British Patent 1523865 describes antiviral purine derivatives with an acyclic chain in the 9-position. Among those derivatives 2-(2-amino-1,6-dihydro-6-oxo-1,6-dihydro-purin-9-yl)methoxy-ethanol with the INN name acyclovir has been found to have good activity against herpes viruses such as herpes simplex. While acyclovir has been found to be very effective upon topical or parenteral administration, it is only moderately absorbed upon oral administration.

U.S. Pat. No. 4,355,032 discloses the compound 9-[(2-hydroxy-1-hydroxymethyl-ethoxy)methyl]-guanine or 2-(2-amino-1,6-dihydro-6-oxo-purin-9-yl)methoxy-1,3-propanediol with the INN name ganciclovir. Ganciclovir is highly efficacious against viruses of the herpes family, for example, against herpes simplex and cytomegalovirus. It has a relatively low rate of absorption when administered orally and must be used at high dosages when administered by that route. Ganciclovir is most commonly administered via intravenous infusion. This mode of administration has the disadvantage of being very inconvenient to the patient, often requiring the services of a doctor, nurse or other health care professional. There is also a certain risk of infection which is particularly problematic for immunocompromised patients who receive treatment with ganciclovir and may have little resistance against infections. Therefore it has been highly desirable to provide ganciclovir with an improved oral absorption profile.

British Patent Application GB 2 122 618 discloses derivatives of 9-(2-hydroxyethoxymethyl)guanine of the generic formula

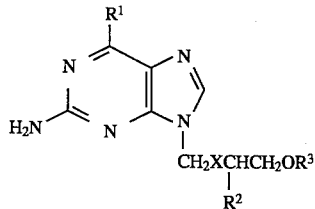

wherein X represents an oxygen or sulphur atom, $R_1$ represents a hydroxy or an amino group, $R^2$ represents a hydrogen atom or a group of the formula —$CH_2OR^3{}_a$ and $R^3$ and $R^3{}_a$ may be the same or different, each represents an amino acid acyl radical and physiologically acceptable salts thereof. These compounds are useful for the treatment of viral infections and have high water solubility which renders them of value in the formulation of aqueous pharmaceutical preparations. While the generic formula in the British patent application includes compounds in which $R^2$ is the group —$CH_2OR^3{}_a$, specific compounds of this group are not disclosed. The patent application also discloses that formulations used with these compounds with improved water-solubility include oral, rectal, nasal, topical, vaginal or parenteral formulations.

British Patent Application GB 2 104 070 A discloses antiviral compounds of the formula

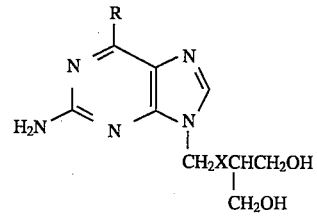

wherein R is a hydroxy or amino group and X is an oxygen or sulphur atom and physiologically acceptable salts and esters. The general formula includes ganciclovir and physiologically acceptable salts and esters. The esters include those containing a formyloxy group, $C_{1-16}$ (for example, $C_{1-6}$) alkanoyloxy (e.g. acetoxy or propionyloxy), optionally substituted aralkanoyloxy (e.g. phenyl-$C_{1-4}$alkanoyloxy such as phenylacetoxy) or optionally substituted aroyloxy (e.g. benzoyloxy or naphthoyloxy) ester grouping at one or both of the terminal positions of the 9-side chain of the compounds of the general formula. The above-mentioned aralkanoyloxy or aroyloxy ester groups may be substituted, for example by one or more halogen (e.g. chlorine or bromo atoms) or amino, nitrile or sulphamido groups, the aryl moiety of the grouping advantageously containing 6 to 10 carbon atoms.

European Patent Application EP 0 375 329 discloses prodrug compounds with the following formula

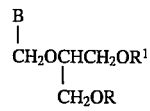

wherein R and $R^1$ are independently selected from a hydrogen atom and an amino acyl residue providing at least one of R and $R^1$ represents an amino acid acyl residue and B represents a group of the formulae

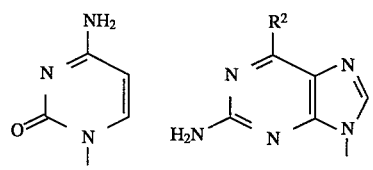

in which $R^2$ represents a $C_{1-6}$ straight chain, $C_{3-6}$ branched chain or $C_{3-6}$ cyclic alkoxy group, or a hydroxy or amino group or a hydrogen atom and the physiologically acceptable salts thereof. These prodrug compounds are described as having advantageous bioavailability when administered the oral route, resulting in high levels of the parent compound in the body.

Example 3 b) European Patent Application EP 0 375 329 discloses the preparation of the bis(L-isoleucinate) ester of ganciclovir as white foam. Example 4 b) discloses the preparation of the bis(glycinate) ester of ganciclovir as a white solid. Example 5 b) discloses the preparation of the bis(L-valinate) ester of ganciclovir as a solid. Example 6 b) discloses the preparation of the bis(L-alaninate) ester of ganciclovir as a syrup containing 90% of the bis ester and 10% of the monoester. The described bis esters are non-crystalline materials which are difficult to process for the manufacture of oral pharmaceutical dosage forms.

E. Jensen et. al., *Acta Pharm. Nord.* 3(4) 243–247 (1991) disclose the synthesis, enzymatic hydrolysis and physico-chemical properties of N-substituted 4-(aminomethyl)benzoate diester prodrugs of ganciclovir of the formula

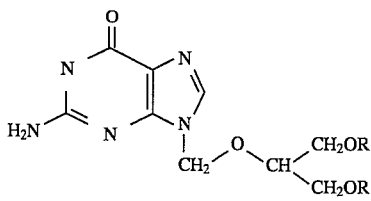

wherein R can be

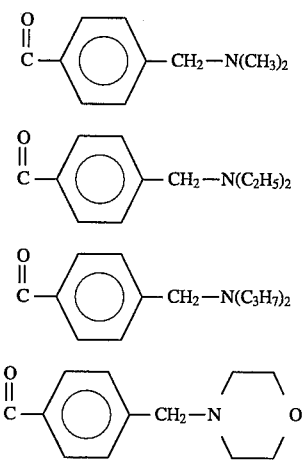

These esters were synthesized and evaluated with the aim of improving the delivery characteristics of ganciclovir. The esters were hydrolyzed enzymatically by human plasma to the parent drug, the hydrolysis proceeding through formation of the corresponding monoester. The authors evaluated these esters in terms of their rate of enzymatic hydrolysis, lipophilicity and concluded that the properties of these esters make the diesters a promising prodrug type for ganciclovir to enhance its delivery characteristics for e.g. parenteral administration.

John C. Martin et. al., *J. Pharm. Sci.* 76(2), p.180–184 disclose mono- and diacyl esters of ganciclovir which were tested to examine their bioavailability after oral administration. The authors indicate that the dipropionate ester is about 42% more bioavailable than ganciclovir itself.

European Patent Application 0 158 847 discloses inter alia that 6-deoxy-acyclovir and 6-deoxy-ganciclovir can be readily converted in vivo by the action of enzymes into acyclovir and ganciclovir, respectively. From experiments in rats the inventors found that oral administration of these 6-deoxy prodrugs results in efficient absorption from the gastro-intestinal tract and high plasma levels of the parent drugs.

P. C. Maudgal et. al., *Arch. Ophthalmol.* 1984; 102: 140–142 disclose the glycine ester of acyclovir as efficacious in the topical treatment of epithelial and stromal herpes simplex keratitis and associated iritis when administered as a 1% eye drop formulation to rabbits. The authors disclose the glycine, alanine, β-alanine and succinyl esters of acyclovir and indicate that the solubility of the glycine ester is about 30-fold greater than the solubility of acyclovir itself, which permits the use of the glycine ester for eye drops with concentrations up to 6%, while acyclovir itself is used as ointment which is hardly effective in stromal disease or iritis.

Leon Colla et. al., *J. Med. Chem.* 98, 3, 26, 602–604 disclose several water-soluble ester derivatives of acyclovir and their salts as prodrugs of acyclovir. The authors indicate that acyclovir cannot be given as eye drops or intramuscular injections because of its limited solubility in water and have therefore synthesized derivatives of acyclovir which are more water soluble than the parent compound. The authors disclose the hydrochloride salt of the glycyl ester, the hydrochloride salt of the alanyl ester, the hydrochloride salt of the β-alanyl ester, the sodium salt of the succinyl ester, and the azidoacetate ester. When assayed in primary rabbit kidney cell cultures against various herpes simplex virus type 1 and type 2 strains, according to the authors, the first four esters proved almost as active as acyclovir itself. The authors suggest that these acyclovir esters should be more practical for clinical use than the parent compound for topical treatment as eye drops and for systemic treatment of herpes virus infections that respond well to intravenous acyclovir treatment. In contrast with acyclovir, these esters could be given in much smaller volumes, and therefore via intramuscular injections.

L. M. Beauchamp et. al., *Antiviral Chemistry & Chemotherapy* (1992), 3 (3), 157–164 disclose eighteen amino acid esters of the antiherpetic drug acyclovir and their efficiencies as prodrugs of acyclovir, evaluated in rats by measuring the urinary recovery of acyclovir. Ten prodrugs produced greater amounts of the parent drug in the urine than acyclovir itself: the glycyl, D,L-alanyl, L-alanyl, L-2-aminobutyrate, D,L-valyl, L-valyl, DL-isoleucyl, L-isoleucyl, L-methionyl, and L-prolyl ester. The L-amino acid esters were better prodrugs than the corresponding D- or D,L-isomers, suggesting the involvement of a stereoselective transporter. From Table 1 of the publication which provides chemical data and oral bioavailability of the eighteen amino acid esters it follows that the D-amino acid esters have a lower oral bioavailability than acyclovir itself. Therefore, because the D-amino acid esters have no benefit over acyclovir they are not useful as prodrugs of acyclovir. The achiral glycyl ester of acyclovir, however, has a 58% higher oral bioavailability than acyclovir (in the urinary recovery assay 30% of the acyclovir dosed as glycyl ester was recovered, whereas with acyclovir dosing 19% of the acyclovir was recovered). According to the authors the L-valyl ester of acyclovir was the best prodrug of the esters investigated.

European Patent Publication 308 065 discloses the valine and isoleucine esters of acyclovir, preferably in the L-form, as showing a large increase in absorption from the gut after oral administration, when compared with other esters and acyclovir.

Japanese Patent Application 05097887 (Derwent 93-164474/20) inter alia discloses certain 2-methyl alanine $[(CH_3)_2—C((—NH_2)—COOH]$ esters of 2'-deoxy-5-fluoro-uridine derivatives as useful antineoplastic agents with low toxicity.

Currently the leading drug for the treatment of cytomegalovirus infection is ganciclovir. However, its very limited oral bioavailability and the need for slow daily intravenous infusion of the drug (or for intravitreal injections or implants) indicate the urgent need for an oral dosage form with improved bioavailability.

The present invention provides a stable prodrug formulation of ganciclovir with improved oral absorption and low toxicity. Such characteristics are especially valuable for suppression of herpetic infections in immunocompromised patients where oral administration therapeutically is the preferred choice. In addition, the active ingredients exhibit pharmacopoeial properties which permit their improved characterization and pharmaceutical processing. Surprisingly, it was found that certain non-natural, achiral amino acid esters with a tertiary α-atom exhibit these desired characteristics.

SUMMARY OF THE INVENTION

In a first aspect, this invention provides a compound of Formula I:

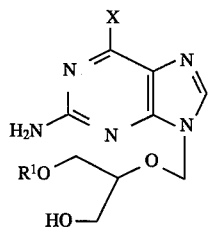

wherein:
X is hydrogen, chloro, amino or hydroxy;
$R^1$ is an achiral amino acid acyl residue with a tertiary α-carbon atom;
or a pharmaceutically acceptable salt thereof. Suitable achiral amino acids have 4 to 16 carbon atoms.

Preferred are compounds of Formula I
wherein:
the achiral amino acid acyl residue has the formula

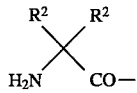

wherein:
each $R^2$ is selected from alkyl with 1 to 6 carbon atoms, cycloalkyl with 3 to 5 carbon atoms, and benzyl; or the two $R^2$ groups link together to form a polymethylene group with 3 to 9 carbon atoms;
or a pharmaceutically acceptable salt thereof.

In a second aspect, this invention provides a pharmaceutical composition which contains a compound of Formula I, preferably in admixture with one or more suitable excipients.

In a third aspect, this invention provides a method of treating or preventing viral infections or related diseases comprising the administration of a compound of Formula I or a composition containing same to an animal in need of such treatment or prevention.

In a fourth aspect, this invention provides compounds of Formula II which are useful intermediates for preparing compounds of Formula I:

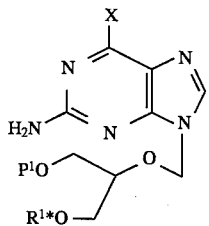

wherein:
X has the above meanings, $P^1$ is a hydroxy-protecting group and $R^{1*}$ is an achiral amino acid acyl residue with a tertiary α-carbon atom having the formula

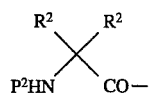

wherein each $R^2$ has the above meanings and $P^2$ is an amino-protecting group.

In a fifth aspect this invention provides compounds of Formula III

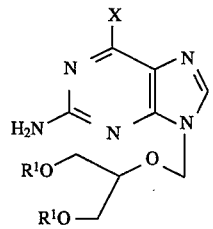

wherein X and $R^1$ have the above meanings. The compounds of Formula III are also useful intermediates for preparing the compounds of Formula I.

A sixth aspect of this invention is a process for preparing the prodrugs of Formula I. This process involves the esterification of ganciclovir and its derivatives, the removal of protecting groups from esterified ganciclovir derivatives, the partial hydrolysis of ganciclovir bis esters to the monoesters of Formula I, the condensation of guanine with a substituted glycerol, the optical resolution of compounds of the Formula I, and the formation of salts of the prodrugs of Formula I. Details of the process are described below.

DETAILED DESCRIPTION OF THE INVENTION

Definitions

Unless otherwise stated, the following terms used in the specification and claims have the meanings given below:

"Alkyl" means a straight or branched, and in general, saturated hydrocarbon radical having from one to the number of carbon atoms designated. For example, $C_{1-7}$ alkyl is alkyl having at least one but no more than seven carbon atoms, e.g. methyl, ethyl, i-propyl, n-propyl, n-butyl, n-pentyl, n-heptyl and the like. However, the compounds of Formula I include achiral amino acid esters the alkyl group of which may include one C=C or C≡C bond.

"Lower alkyl" means an alkyl of one to six carbon atoms.

"Cycloalkyl" means a cyclic, and in general, saturated hydrocarbon radical having from three to the number of carbon atoms designated. For example, $C_{3-7}$ cycloalkyl is cycloalkyl having at least three but no more than seven carbon atoms, e.g., cyclopropyl, cyclobutyl, cyclopentyl, cyclohexyl or cycloheptyl.

"Lower cycloalkyl" means a cycloalkyl group of three to six carbon atoms.

"Polymethylene" is a divalent group of the formula —$(CH_2)_n$— in which n is an integer from 3 to 9 which optionally includes polymethylene groups with one C=C bond.

"Aryl" means an organic radical derived from an aromatic hydrocarbon by the removal of one hydrogen atom. Preferred aryl radicals have six to twelve carbon atoms as ring carbon atoms in the aromatic hydrocarbon.

"Aralkyl" means an organic radical derived from an aralkane in which an alkyl hydrogen atom is substituted by an above-defined aryl group.

"Acyl" means an organic radical derived from an organic acid by the removal of the hydroxyl group; e.g., RCO— is the acyl radical of RCOOH, whereby R is, as above defined, an alkyl, cycloalkyl, aryl or aralkyl group which optionally may be substituted with one ore two substituents such as amino, lower alkyl, cycloalkyl, lower alkoxy, or benzyl. Examples for such acyl groups are acetyl, propionyl, benzoyl or 1-amino-cyclohexanecarbonyl, etc. The term "acyl" includes the term "alkanoyl" which is the organic radical RCO— in which R is an alkyl or cycloalkyl group as defined above.

"Lower alkoxy" or "RO—", "(lower alkyl)amino" or "(R)NH—", "di(lower alkyl)amino" or "(R)$_2$NH—", "(lower alkanoyl)amino" or "(RCO)NH—", and similar terms mean alkoxy, alkylamino, dialkylamino, alkanoylamino, respectively, in which the or each alkyl (R) radical is a "lower alkyl" as described above.

"Halogen" means fluorine, chlorine, bromine, or iodine.

According to Hackh's *Chemical Dictionary,* McGraw-Hill Book Company, 1969, "derivative" of a compound means a compound obtainable from the original compound by a simple chemical process. Examples of derivatives of guanine are 2-aminopurine and 2,6-diaminopurine and 2-amino-6-chloropurine which are obtainable from guanine by reduction and chlorination, and substitution with an amino group, respectively. These conversions are described in "*Synthetic Procedures in Nucleic Acid Chemistry*", Vol. 1 and 2, W. W. Zorbach and R. S. Tipson, Eds. Wiley Interscience, N.Y. 1968, 1973; *Chemistry of Nucleosides and Nucleotides,* Vol. 1 and 2; L. B. Townsend Ed., Plenum Press, N.Y. 1988 and 1991; and *Nucleic Acid Chemistry,* Part 3 and Part 4; L. B. Townsend and R. S. Tipson, Eds.; J. Wiley & Sons, New York, 1986 and 1991, all incorporated herein by reference. These conversions in position 6 of the purine ring system can also be utilized to convert one compound of the Formula I into another compound of Formula I.

"Activated derivative" of a compound means a reactive form of the original compound which renders the compound active in a desired chemical reaction, in which the original compound is only moderately reactive or non-reactive. Activation is achieved by formation of a derivative or a chemical grouping within the molecule with a higher free energy content than that of the original compound, which renders the activated form more susceptible to react with another reagent. In the context of the present invention activation of the carboxy group is of particular importance and corresponding activating agents or groupings which activate the carboxy group are described in more detail below. For example, an amino acid anhydride is an activated form of an amino acid which renders the amino acid susceptible to esterification.

"Protecting group" means a chemical group that (a) preserves a reactive group from participating in an undesirable chemical reaction; and (b) can be easily removed after protection of the reactive group is no longer required. For example, the benzyl group is a protecting group for a primary hydroxyl function.

"Amino-protecting group" means a protecting group that preserves a reactive amino group that otherwise would be modified by certain chemical reactions. The definition includes the formyl group or lower alkanoyl groups with 2 to 4 carbon atoms, in particular the acetyl or propionyl group, the trityl or substituted trityl groups, such as the monomethoxytrityl group, dimethoxytrityl groups such as the 4,4'-dimethoxytrityl or 4,4'-dimethoxytriphenylmethyl group, the trifluoroacetyl, and the N-(9-fluorenylmethoxycarbonyl) or "FMOC" group, the allyloxycarbonyl group or other protecting groups derived from halocarbonates such as ($C_6$–$C_{12}$)aryl lower alkyl carbonates (such as the N-benzyloxycarbonyl group derived from benzylchlorocarbonate), or derived from biphenylalkyl halo carbonates, or tertiary alkyl halo carbonates, such as tertiary-butylhalocarbonates, in particular tertiary butylchlorocarbonate, or di(lower)alkyldicarbonates, in particular di(t-butyl)dicarbonate, and the phthalyl group.

"Hydroxy-protecting group" means a protecting group that preserves a hydroxy group that otherwise would be modified by certain chemical reactions. Suitable hydroxy-protecting groups include ether-forming groups that can be removed easily after completion of all other reaction steps, such as the benzyl or the trityl group optionally substituted in their phenyl ring. Other suitable hydroxy-protecting groups include alkyl ether groups, the tetrahydropyranyl, silyl, trialkylsilyl ether groups and the allyl group.

"Leaving group" means a labile group that is replaced in a chemical reaction by another group. Examples of leaving groups are halogen, the optionally substituted benzyloxy group, the isopropyloxy group, the mesyloxy group, the tosyloxy group or the acyloxy group.

The term "chirality" means the property of handedness ascribed to a molecule, which describes the symmetry elements of the molecule (or the absence of symmetry elements). Molecules that lack symmetry elements are "chiral". A chiral molecule lacking all of the symmetry elements, even including a simple axis, is termed "asymmetric".

The term "achiral" means the presence of at least one symmetry element in a molecule, such as a simple axis.

The compounds of Formula I and the compounds of Formula II exist as optical isomers, or as mixtures of such isomers. In the compounds of the invention, any isomer or mixture of isomers may be used and the claims are intended to cover each individual isomer and mixtures thereof, unless otherwise restricted. The invention includes all optical isomers of any asymmetrical compound of Formula I, as well as mixtures thereof.

"Isomerism" refers to compounds having the same atomic mass and atomic number but differing in one or more physical or chemical properties. Various types of isomers include the following:

"Stereoisomer" refers to a chemical compound having the same molecular weight, chemical composition, and constitution as another, but with the atoms grouped differently. That is, certain identical chemical moieties are at different orientations in space and, therefore, when pure, have the ability to rotate the plane of polarized light. However, some pure stereoisomers may have an optical rotation that is so slight that it is undetectable with present instrumentation.

"Optical isomer" describes one type of stereo isomerism which manifests itself by the rotation that the isomer, either pure or in solution, imparts to the plane of polarized light. It is caused in many instances by the attachment of four different chemical atoms or groups to at least one of the carbon atoms in a molecule, or expressed alternatively, by the above-described chirality of the molecule.

Stereoisomers or optical isomers that are mirror images of one another are termed "enantiomers" and may be said to be enantiomeric. Chiral groups that are mirror images of one another are termed enantiomeric groups.

Enantiomers whose absolute configurations are not known may be differentiated as dextrorotatory (prefix +) or laevorotatory (prefix −) depending on the direction in which, under specified experimental conditions, they rotate the plane of polarized light.

When equal amounts of enantiomeric molecules are present together, the product is termed racemic, independently of whether it is crystalline, liquid, or gaseous. A homogeneous solid phase composed of equimolar amounts of enantiomeric molecules is termed a racemic compound. A mixture of equimolar amounts of enantiomeric molecules present as separate solid phases is termed a racemic mixture. Any homogeneous phase containing equimolar amounts of enantiomeric molecules is termed a racemate.

The optically active compounds herein can be designated by a number of conventions; i.e., the R- and S-sequencing rules of Cahn and Prelog; erythro and threo isomers; D and L-isomers; d and l-isomers; which indicates the direction a plane of polarized light is rotated by the chemical structure, either pure or in solution. These conventions are well known in the art and are described in detail by E. L. Eliel in *Stereochemistry of Carbon Compounds,* published by McGraw Hill Book Company, Inc. of New York in 1962 and references cited therein. Thus, these isomers may be described as d-, l-, or a d,l-pair; or D-, L-, or a D,L-pair; or R-, S-, or an R,S-pair; depending upon the nomenclature system employed. Unless indicated otherwise, this application will use the (R), (S) and (R,S) designations.

"Optional" or "optionally" means that the subsequently described event or circumstance may or may not occur, and that the description includes instances where said event or circumstance occurs and instances in which it does not. For example, "optionally substituted phenyl" means that the phenyl may or may not be substituted and that the description includes both unsubstituted phenyl and phenyl wherein there is substitution; "reacting a compound optionally protected in the 2-position" means that the compound undergoing said reaction may or may not include a protecting group in the 2-position, and the invention includes those processes wherein the 2-position is protected and those processes in which it is not.

"Pharmaceutically acceptable" means that which is useful in preparing a pharmaceutical composition that is generally safe and non-toxic and includes that which is acceptable for veterinary use as well as human pharmaceutical use.

"Pharmaceutically acceptable salts" means salts which possess the desired pharmacological activity and which are neither biologically nor otherwise undesirable. Such salts include acid addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxy-benzoyl)-benzoic acid, cinnamic acid, mandelic acid, methanesulfonic acid, ethanesulfonic acid, 1,2-ethanedisulfonic acid, 2-hydroxyethane-sulfonic acid, benzenesulfonic acid, p-chlorobenzenesulfonic acid, 2-naphthalenesulfonic acid, p-toluenesulfonic acid, camphorsulfonic acid, 4-methyl-bicyclo[2.2.2]oct-2-ene-1-carboxylic acid, gluco-heptonic acid, 4,4'-methylenebis(3-hydroxy-2-naphthoic) acid, 3-phenylpropionic acid, trimethylacetic acid, tertiary butylacetic acid, lauryl sulfuric acid, gluconic acid, glutamic acid, hydroxy-naphthoic acids, salicylic acid, stearic acid, muconic acid, and the like. Preferred pharmaceutically acceptable salts are those formed with hydrochloric, sulfuric, phosphoric acid, acetic or methanesulfonic acid, ethanesulfonic acid, 1,2-ethanedisulfonic acid, 2-hydroxyethanesulfonic acid, benzenesulfonic acid, p-chlorobenzenesulfonic acid, and 2-naphthalenesulfonic acid, p-toluenesulfonic acid, and camphorsulfonic acid.

Synthetic Reaction Parameters

Unless specified to the contrary, the reactions described herein take place at atmospheric pressure within a temperature range from 5° C. to 170° C. (preferably from 10° C. to 50° C.; most preferably at "room" or "ambient" temperature, e.g., 20°–30° C.). However, there are clearly some reactions where the temperature range used in the chemical reaction will be above or below these temperature ranges. Further, unless otherwise specified, the reaction times and conditions are intended to be approximate, e.g., taking place at about atmospheric pressure within a temperature range of about 5° C. to about 100° C. (preferably from about 10° C. to about 50° C.; most preferably about 20° C.) over a period of about 1 to about 100 hours (preferably about 5 to 60 hours). Parameters given in the Examples are intended to be specific, not approximate.

Isolation and purification of the compounds and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples hereinbelow. However, other equivalent separation or isolation procedures can, of course, also be used.

Medical Definitions

"Animal" includes humans, non-human mammals (such as dogs, cats, rabbits, cattle, horses, sheep, goats, swine, and deer) and non-mammals such as birds, fish and the like.

"Disease" specifically includes any unhealthy condition of an animal or part thereof. Thus, "disease" here includes any viral or related disease that is treatable with a compound of the Formula I or pharmaceutically acceptable salts thereof.

"Treatment" means any treatment of a disease in an animal and includes:

(1) preventing the disease from occurring in an animal which may be predisposed to the disease but does not yet experience or display symptoms of the disease; e.g. prevention of the outbreak of the clinical symptoms;

(2) inhibiting the disease, e.g. arresting its development; or (3) relieving the disease, e.g. causing regression of the symptoms.

"Effective amount" for the treatment of a disease means that amount which, when administered to an animal in need thereof, is sufficient to effect treatment, as defined above, for that disease.

Nomenclature

The compounds of Formula I, II and III are named in accordance with generally acceptable nomenclature rules.

The compound of the following formula

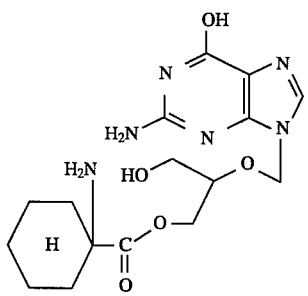

is named 2-(2-amino-1,6-dihydro-6-oxo-purin-9-yl) methoxy-3-hydroxy-1-propanyl (1-amino-cyclohexanecarboxylate). Its (R)-enantiomer is named (R)-2-(2-amino-1,6-dihydro-6-oxo-purin-9-yl)methoxy-3-hydroxy-1-propanyl (1-amino-cyclohexanecarboxylate).

The compound of the following formula

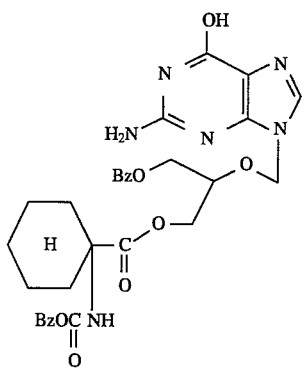

is named 2-(2-amino-1,6-dihydro-6-oxo-purin-9-yl) methoxy-1-benzyloxy-3-propanyl (N-benzyloxycarbonyl-1-amino-cyclohexanecarboxylate).

The compound of the following formula

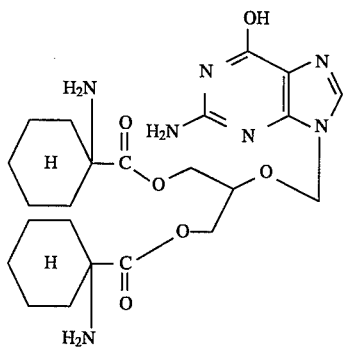

is named 2-(2-amino-1,6-dihydro-6-oxo-purin-9-yl) methoxy-1,3-propanediyl bis(1-amino-cyclohexanecarboxylate).

The compound of the following formula

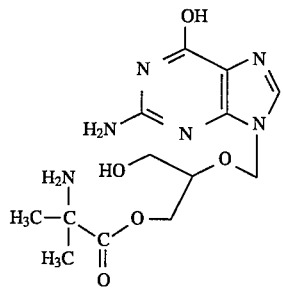

is named 2-(2-amino-1,6-dihydro-6-oxo-purin-9-yl) methoxy-3-hydroxy-1-propanyl (2-amino-2-methyl-propionate).

The compound of the formula

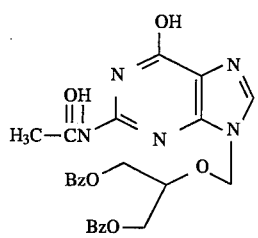

is named N2-Acetyl-2-(2-amino-1,6-dihydro-6-oxo-purin-9-yl)methoxy-1,3-bis(benzyloxy)-propane or N2-acetyl-bis-O-benzyl-ganciclovir.

Processes for Preparing Compounds of the Invention

The compounds of Formula I are prepared by a variety of methods. The synthetic approaches are apparent from the labelled dotted lines [(a) through (i)] in Formula I below. The dotted lines point schematically to the respective reaction sites and the ensuing table gives a brief description of the various methods that will be described in more detail below. The letter symbols in parentheses refer to the respective step in the process description/claim(s):

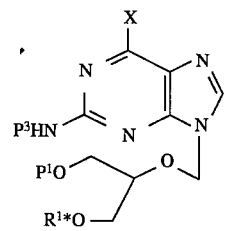

| Approach | Method |
| --- | --- |
| (a) | De-protection |
| (b) | Salt Formation |
| (c) | Esterification |
| (d) | Condensation |
| (e) | Partial Hydrolysis |
| (f), (g), (h) in 6-Position | Conversion of Substituent |
| (i) | Optical Resolution |

Accordingly, the process for the preparation of the compounds of Formula I (wherein X, $R^1$ and $R^2$ have the above meanings), or a pharmaceutically acceptable salt thereof comprises one or more of the following steps:

(a) removal of an amino- and/or hydroxy-protecting group from a compound with the Formula II A

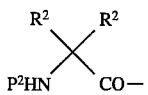

wherein:

X has the above meanings, $P^1$ is hydrogen or a hydroxy-protecting group, $R^{1*}$ is an achiral amino acid acyl residue with a tertiary α-carbon atom, having the formula $$\begin{array}{cc} R^2 & R^2 \\ \diagdown \!\!\! \diagup \\ P^2HN \quad CO- \end{array}$$

wherein each $R^2$ has the above meanings and $P^2$ is an amino-protecting group, and $P^3$ is hydrogen or $P^2$, to afford a compound of Formula I;

(b) conversion of a compound of Formula I into a pharmaceutically acceptable salt thereof;

(c) esterification of a compound of Formula I*

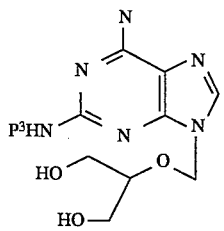

or a salt thereof, wherein X has the above meanings, and $P^3$ is hydrogen or $P^2$, with a derivative of an amino acid of the Formula IV

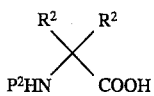

wherein each $R^2$ has the above meanings and $P^2$ is an amino-protecting group;

(d) condensation of an optionally substituted guanine of the Formula V

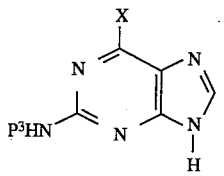

optionally in persilylated form,
wherein X has the above meanings and $P^3$ is hydrogen or an amino-protecting group, with a 2-substituted glycerol of the Formula VI

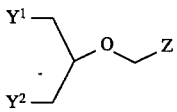

wherein $Y^1$ and $Y^2$ independently are halo, lower acyloxy or lower alkoxy, or aralkyloxy groups, and Z is a leaving group selected from lower acyloxy, methoxy, isopropyloxy, benzyloxy, halo, mesyloxy or tosyloxy and the like; optionally in the presence of a Lewis acid catalyst to afford a compound of Formula I;

(e) partial hydrolysis of a compound of Formula III

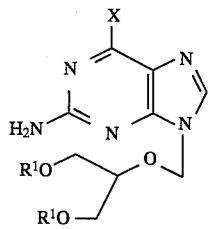

wherein X and $R^1$ have the above meanings to afford a compound of Formula I;

(f) conversion of a compound of the Formula I, wherein X is hydrogen, to a compound of Formula I, wherein X is hydroxy or chloro, (g) conversion of a compound of Formula I, where X is chloro, to a compound of Formula I, wherein X is hydrogen; or (h) conversion of a compound of Formula I, wherein X is hydroxy, to a compound of Formula I, wherein X is chloro; and (i) optical resolution of a compound of Formula I into its enantiomers.

Utility and Testing

The compounds of this invention, as defined by Formula I, exhibit pharmaceutical activity and in particular antiviral activity. As such, these compounds are useful for treating a broad range of conditions in animals, particularly humans.

Examples of conditions that may be treated using the compounds of this invention include herpes infections such as herpes types 1, 2 and 6, varicella Zoster, Eppstein-Barr virus, in particular cytomegalovirus, and hepatitis B and related viruses, in humans or non-human animals, particularly in humans. Examples of clinical conditions caused by these viruses are herpetic keratitis, herpetic encephalitis, cold sores, genital infections (caused by herpes simplex), chicken pox, shingles (caused by varicella Zoster), CMV-pneumonia and -retinitis, particularly in immunocompromised patients including transplant recipients (for example, heart, renal and bone marrow transplants) and patients with Acquired Immune Deficiency Syndrome (AIDS), Eppstein-Barr virus-caused infectious mononucleosis. The compounds of the invention are also useful for the treatment of certain carcinomas or lymphomas caused by, or related to, viral infections, such as nasopharyngeal cancer, immunoblastic lymphoma, Burkitt's lymphoma, and hairy leukoplakia.

In summary, then another aspect of this invention is a method for treating an animal (preferably a human) exhibiting a condition in which an above-described viral or related infection plays a role, or prophylactically treating an animal where such viral infection is anticipated by the treating physician or veterinarian. The method comprises administering a therapeutically effective amount of a compound of Formula I to such animal. The exact amount administered may vary over a wide range depending on the degree of severity of the specific condition being treated, age of the subject, relative health of the subject and other factors (such as type of formulation). For an oral formulation a therapeutically effective amount may vary from about 1 to 250 mg per Kg body weight per day, preferably about 7 to 100 mg/Kg body weight per day. Most preferably the therapeutically effective amount is about 10 to 50 mg/Kg/day, especially for the treatment of CMV retinitis and pneumonia. Thus, for a 70 Kg human, a therapeutically effective amount may be from about 70 mg/day to about 7 g/day, preferably about 500 mg/day to about 5 g/day, most preferably 700 mg/day to 3.5 g/day. For an intravitreal implant, however, the dose of the prodrug will range from 0.5 mg to 25 mg, preferably from 5 to 10 mg per implant. It is well understood by those skilled in the art that different dosage forms of the prodrugs of the invention will command different dosage ranges.

Some of the compounds of Formula III have also antiviral activity. We have found that the monoesters of the Formula I are substantially more active compounds than the corresponding bis-esters of Formula III. However, all compounds of Formula III are useful intermediates for the preparation of the compounds of Formula I.

Ganciclovir is a proven antiviral drug. The utility of the ganciclovir prodrugs of the present invention has been established by determining the blood level concentrations of ganciclovir in test animals (the rat and the monkey), following oral administration of these prodrugs. The blood plasma level concentrations were determined according to the methods described in Examples 8 and 9 and are procedures which modify procedures described by Jean-Pierre Sommadossi et. al. in *REVIEWS OF INFECTIOUS DISEASES*, VOL. 10, SUPPLEMENT 3, p. S507 and in *Journal of Chromatography, Biomedical Applications*, 414 (1987), 429–433.

Administration and Pharmaceutical Compositions

The compounds of this invention may be administered via any of the usual and acceptable modes known in the art, either singly or in combination with another compound of this invention or with another therapeutic agent. Generally a compound of this invention is administered as a pharmaceutical composition with a pharmaceutically acceptable excipient and is administered orally, systemically (e.g. transdermally, or by suppository) or parenterally (e.g. intramuscularly [im], intravenously [iv], subcutaneously [sc]) or intravitreally by an implant. The compounds of the invention are particularly well suited for oral administration. The compounds of the invention can thus be administered in a composition that is a semisolid, powder, aerosol, solution, suspension or other appropriate composition, as discussed hereinafter.

A pharmaceutical composition comprises a compound of Formula I or III, wherein each substituent is defined hereinabove, preferably in combination with a pharmaceutically acceptable excipient. Such excipient is one that is non-toxic in the administration of the compound of this invention. Such excipient may be any solid, liquid, semisolid, gaseous (in case of an aerosol) excipient that is generally available to one of skill in the art and that does not adversely affect the activity of the active agent.

In general, the pharmaceutical composition of this invention will contain a therapeutically effective amount of a compound in combination with at least one excipient. Depending on the type of formulation, size of a unit dosage, kind of excipients and other factors known to those of skill in the art of pharmaceutical sciences the amount of compound of this invention may vary over a wide range in the composition. In general, the final composition will comprise about 1% to about 99.5% wt of a compound of the invention with the remainder being the excipient or excipients. Preferably the level of active compound will be about 10% wt to about 99% wt and most preferably about 50% wt to about 99% wt, with the remainder being a suitable excipient or excipients. Useful pharmaceutical excipients for the preparation of the pharmaceutical compositions hereof can be solids, semisolids, liquids or gases. Thus, the compositions can take the form of tablets, pills, capsules, powders, suppositories, transdermal patches, intravitreal implants, sustained release formulations, solutions, suspensions, elixirs, aerosols, and the like. Solid pharmaceutical excipients include starches, such as corn starch, cellulose, talc, glucose, lactose, sucrose, gelatin, malt, rice, flour, chalk, silica gel, magnesium stearate, sodium stearate, stearic acid, glycerol monostearate, sodium chloride, dried skim milk, and the like. Liquid and semisolid excipients may be selected from water, ethanol, glycerol, propylene glycol, various oils, including those of petroleum, animal, vegetable or synthetic origin, for example, peanut oil, soybean oil, mineral oil, sesame oil, and the like. Water, saline, aqueous dextrose, and glycols are preferred liquid carriers, particularly for injectable solutions. Other suitable pharmaceutical excipients, carriers and their formulations are described in *"Remington's Pharmaceutical Sciences"* by E. W. Martin, incorporated herein by reference.

Preferably the pharmaceutical composition is administered in a single unit dosage form, more preferably an oral dosage form, for continuous treatment or in a single unit dosage form ad libitum when relief of symptoms is specifically required.

Presently Preferred Embodiments

While the broadest definition of this invention is set forth in the Summary of the Invention as a compound of Formula I wherein each of X, $R^1$ and $R^2$ is defined in its broadest aspect, certain compounds of the invention are preferred.

Preferred are compounds of Formula I wherein each $R^2$ is methyl, ethyl, propyl, cycloalkyl with 3 to 5 carbon atoms; or the two $R^2$ groups linked together form a polymethylene group with 3 to 9 carbon atoms; or pharmaceutically acceptable salts thereof. Of these, preferred are compounds of Formula I wherein X is hydroxy; and the two $R_2$ groups linked together form a polymethylene group with 3 to 9 carbon atoms; or pharmaceutically acceptable salts thereof. Of these, even more preferred are compounds of Formula I wherein X is hydroxy. Most preferred are the compounds of Formula I wherein X is hydroxy and the two $R_2$ groups linked together form a polymethylene group with 4 or 5 carbon atoms; or pharmaceutically acceptable salts thereof.

The following acids are preferred to form pharmaceutically acceptable salts with the compounds of Formula I: hydrochloric, sulfuric, phosphoric acid, acetic, methanesulfonic, ethanesulfonic, 1,2-ethanedisulfonic, 2-hydroxyethanesulfonic, benzenesulfonic, p-chlorobenzenesulfonic, 2-naphthalenesulfonic, p-toluenesulfonic and camphorsulfonic acid. Most preferred are strong inorganic acids.

Preferred are the following specific compounds:

2-(2-amino-1,6-dihydro-6-oxo-purin-9-yl)methoxy-3-hydroxy-1-propanyl (1-amino-cyclooctanecarboxylate) and its pharmaceutically acceptable salts;

2-(2-amino-1,6-dihydro-6-oxo-purin-9-yl)methoxy-3-hydroxy-1-propanyl (1-amino-cycloheptanecarboxylate) and its pharmaceutically acceptable salts;

2-(2-amino-1,6-dihydro-6-oxo-purin-9-yl)methoxy-3-hydroxy-1-propanyl (1-amino-cyclohexanecarboxylate) and its pharmaceutically acceptable salts;

2-(2-amino-1,6-dihydro-6-oxo-purin-9-yl)methoxy-3-hydroxy-1-propanyl (1-amino-cyclopentanecarboxylate) and its pharmaceutically acceptable salts;

2-(2-amino-1,6-dihydro-6-oxo-purin-9-yl)methoxy-3-hydroxy-1-propanyl (1-amino-cyclobutanecarboxylate) and its pharmaceutically acceptable salts;

2-(2-amino-1,6-dihydro-6-oxo-purin-9-yl)methoxy-3-hydroxy-1-propanyl (2-amino-2-methylpropionate) and its pharmaceutically acceptable salts;

2-(2-amino-1,6-dihydro-6-oxo-purin-9-yl)methoxy-3-hydroxy-1-propanyl (2-amino-2-ethylbutyrate) and its pharmaceutically acceptable salts; and 2-(2-amino-1,6-dihydro-6-oxo-purin-9-yl)methoxy-3-hydroxy-1-propanyl (2-amino-2-n-propylvalerate) and its pharmaceutically acceptable salts.

The most preferred compounds are:

2-(2-amino-1,6-dihydro-6-oxo-purin-9-yl)methoxy-3-hydroxy-1-propanyl (1-amino-cyclohexanecarboxylate) and its pharmaceutically acceptable salts, especially the hydrochloride;

2-(2-amino-1,6-dihydro-6-oxo-purin-9-yl)methoxy-3-hydroxy-1-propanyl (1-amino-cyclopentanecarboxylate) and its pharmaceutically acceptable salts, especially the hydrochloride;

2-(2-amino-1,6-dihydro-6-oxo-purin-9-yl)methoxy-3-hydroxy-1-propanyl (1-amino-cyclobutanecarboxylate) and its pharmaceutically acceptable salts, especially the hydrochloride;

2-(2-amino-1,6-dihydro-6-oxo-purin-9-yl)methoxy-3-hydroxy-1-propanyl (2-amino-2-methylpropionate) and its pharmaceutically acceptable salts, especially the hydrochloride;

2-(2-amino-1,6-dihydro-6-oxo-purin-9-yl)methoxy-3-hydroxy-1-propanyl (2-amino-2-ethylbutyrate) and its pharmaceutically acceptable salts, especially the hydrochloride; and 2-(2-amino-1,6-dihydro-6-oxo-purin-9-yl)methoxy-3-hydroxy-1-propanyl (2-amino-2-n-propylvalerate) and its pharmaceutically acceptable salts, especially the hydrochloride.

It is understood that these subgroups of particular interest and these specific compounds are particularly useful in the pharmaceutical compositions and methods of treatment of this invention.

In any of the above last step processes described herein a reference to Formula I, I*, II, III, IV, V and VI refers to such Formulae wherein $R^1$, $R^{1*}$ and $R^2$, $P^1$, $P^2$, and $P^3$ and X, $Y^1$, $Y^2$, and Z are as defined in their broadest definitions set forth in the Summary of the Invention, with the processes applying particularly to the presently preferred embodiments.

The preferred pharmaceutical compositions of this invention contain a pharmaceutically acceptable salt of the prodrugs of Formula I. Accordingly, if the manufacture of pharmaceutical formulations involves intimate mixing of the pharmaceutical excipients and the active ingredient in its salt form, then it is preferred to use pharmaceutical excipients which are nonbasic in nature, i.e., either acidic or neutral.

Details of the Synthetic Processes

The currently preferred process for producing a compound of the Formula I involves step (a), preferably carried out with the concomitant formation of a salt of a compound of Formula I, or step (c), or a combination of steps (a) and (c). (See the description of Steps III and IV below). The preparation of the monoesters according to step (a) requires the selective protection of one of the two primary hydroxyl functions of ganciclovir or its derivative. This generally may or may not involve protection of the amino group in the 2-position of the guanine base (see the detailed description below of Steps I through III for the case the process is carried out with a protected amino group). In addition, before the esterification (Step III) is carried out, the amino group of the amino acid reagent must be protected, to avoid its interference (amide formation) in the esterification reaction. The protection of the amino group is described in the section "Preparation of the N-Protected Amino Acid" below.

In general, when carrying out a process of this invention, those amino or hydroxy groups which are not to participate in the synthesis reaction must be protected until (1) either de-protection yields the final product; or (2) a specific protected group is to be involved in the next synthetic step; or (3) the presence of the unprotected group in the ensuing reaction steps leading to the final product would not modify the intended sequence of reactions. An example for meeting requirement (1) is the benzyl group in the preparation of the monoesters of this invention, which protects one primary hydroxyl function of ganciclovir until it is removed in the deprotection. An example for meeting requirement (2) is the second benzyl group protecting the second primary hydroxyl function of ganciclovir which is removed just prior to the esterification step. An example for meeting requirement (3) is the acetyl group, or the trityl or monomethoxytrityl group protecting the amino group of the guanine ring system of ganciclovir, as the unprotected amino group does not interfere with the esterification (step III).

In general, the qualification of potential blocking agents that render them suitable for use in the preparation of the compounds of Formula I include:

(1) Their introduction should proceed quantitatively and smoothly;

(2) The blocked intermediate must be stable to conditions of the reactions employed until removal of the protecting group is required;

(3) The blocking group must be susceptible of being readily removed under conditions which do not change the chemical nature of the remainder of the molecule.

Starting Materials

The acyclic achiral amino acids employed to prepare the mono- and diesters of the Formulae I and III are known compounds or can be made by known methods. See *Chem. Commun.* 1966 (1), 12–13; *Int. J. Pept. Protein Res.*, 21(4), 406–418, 1983; and ibid. 21(4), 392–405, 1983; *Pept., Proc. Eur. Pept. Symp.*, 20th, Meeting Date 1988, 13–15; *J. Org. Chem.* 22, 799–802 (1957); *Pept.* 1990, *Proc. Eur. Pept. Symp.*, 21 st, Meeting Date 1990, 41–42, *Can. J. Chem.* 37, 1309–20 (1961); *J. Med. Pharm. Chem.* 3, 1–23 (1961). All these references are incorporated by reference herein.

The selection of the achiral amino acid for the preparation of the amino acid esters of the Formula I is critical as the amino acid component confers improved bioavailability, in particular oral bioavailability, to the compounds of the invention. Achiral amino acids which are useful for the preparation of the compounds of Formula I include 1-amino-cyclohexanecarboxylic acid;
1-amino-cyclopentanecarboxylic acid;
1-amino-cyclobutanecarboxylic acid;
1-amino-cycloheptanecarboxylic acid;
1-amino-cyclooctanecarboxylic acid;
1-amino-cyclononanecarboxylic acid;
1-amino-cyclodecanecarboxylic acid;
2-amino-2-methylpropionic acid;
2-amino-2-ethylbutyric acid;
2-amino-2-n-propylvaleric acid;
2-amino-2-isopropyl-3-methylbutyric acid;
2-amino-2-isobutyl-4-methylvaleric acid;
2-amino-2-n-butylhexanoic acid;
2-amino-2,2-biscyclopropylacetic acid;
2-amino-2,2-biscyclobutylacetic acid; and
2-amino-2,2-bisbenzylacetic acid.

A preferred protected ganciclovir starting material for the preparation of the preferred compounds of the invention is N2-acetyl-bis-O-benzyl-ganciclovir (N2-acetyl-2-(2-amino-1,6-dihydro-6-oxo-purin-9-yl)methoxy-1,3-bis(benzyloxy)propane) which is described in U.S. Pat. No. 4,355,032. Other preferred protected ganciclovir starting materials are $N^2$-trityl-9-[(3-hydroxy-2-propoxy-1-trityloxy)methyl]guanine [$N^2$-trityl-2-(2-amino-1,6-dihydro-6-oxo-purin-9-yl)methoxy-1-trityloxy-propan-3-ol] and $N^2$-monomethoxytrityl-9-[(3-hydroxy-2-propoxy-1-monomethoxytrityloxy)methyl]guanine, the preparation of which is described in *J. Pharm. Sci.* 76(2), p.180–184 (1987) which is incorporated herein by reference.

The intermediates of Formula III may be prepared by esterifying ganciclovir (optionally with a protected 6-amino group) with at least two equivalents, preferably 3 equivalents, of the compound of Formula IV under conditions described herein for the preparation of the monoesters of Formula I, that is in the presence of an activating agent at temperatures between 0° and 50°, preferably 20°–40° C. A detailed procedure is described in Example 6. Alternatively, the compounds of Formula III can be prepared according to the process described in European Patent Publication 0 375 329. Preferred starting materials of Formula III are:

2-(2-amino-1,6-dihydro-6-oxo-purin-9-yl)methoxy-1,3-propanediyl bis (1-amino-cyclohexanecarboxylate) and its salts;

2-(2-amino-1,6-dihydro-6-oxo-purin-9-yl)methoxy-1,3-propanediyl bis (1-amino-cyclopentanecarboxylate) and its salts;

2-(2-amino-1,6-dihydro-6-oxo-purin-9-yl)methoxy-1,3-propanediyl bis (1-amino-cyclobutanecarboxylate) and its salts;

2-(2-amino-1,6-dihydro-6-oxo-purin-9-yl)methoxy-1,3-propanediyl bis (2-amino-2-methylpropionate) and its salts;

2-(2-amino-1,6-dihydro-6-oxo-purin-9-yl)methoxy-1,3-propanediyl (2-amino-2-ethylbutyrate) and its salts; and 2-(2-amino-1,6-dihydro-6-oxo-purin-9-yl)methoxy-1,3-propanediyl bis (2-amino-2-n-propylvalerate) and its salts.

It is to be understood that the intermediates of Formula III can be used as free bases or in the form of any salt (not only in the form of a pharmaceutically acceptable salt) that is useful to achieve the desired partial hydrolysis to the monoesters of Formula I. However, it is preferred to use pharmaceutically acceptable salts of the compounds of Formula III.

Preparation of the N-Protected Amino Acid of the Formula IV

Prior to carrying out the esterification step, the amino group of the amino acid must be protected to avoid undesirable amide formation. The following amino-protecting groups are useful: halocarbonates such as ($C_6$–$C_{12}$)aryl lower alkyl carbonates (such as the carbobenzyloxy group derived from benzylchlorocarbonate), or biphenylalkyl halo carbonates, or tertiary alkyl halo carbonates, such as tertiary-butylhalocarbonates, in particular tertiary butylchlorocarbonate, or di(lower)alkyldicarbonates, in particular di(t-butyl)dicarbonate, triphenylmethyl halides such as triphenylmethyl chloride, and trifluoroacetic anhydride. The protecting step is carried out by dissolving or suspending the amino acid in an alkaline aqueous solution which may include a lower alkanol. The reaction mixture is cooled while the protecting reagent such as the halocarbonate, preferably in an aqueous or lower alkanol solution is added simultaneously in small portions. During this addition, the reaction mixture is kept at 0° to 30°, preferably 0°–5° C. with an ice bath for several hours. Then the ice bath is removed and the mixture kept at room temperature until it reaches room temperature. The reaction mixture is concentrated to dryness and the residue is partitioned between an organic phase and water. The aqueous layer is acidified and extracted with an organic solvent for the protected amino acid. The organic phase is washed with water followed by brine washings and dried over magnesium sulfate before evaporation to dryness, and the N-protected amino acid of Formula IV isolated and purified by conventional techniques.

Preparation of the Monoesters of the Formula I

Step I: Ganciclovir, with an optionally protected 2-amino group and both primary hydroxyl functions protected is partially de-protected. N2-Acetyl-bis-O-benzyl-ganciclovir (according to the nomenclature used herein: N2-acetyl-2-(2-amino-1,6-dihydro-6-oxo-purin-9-yl)methoxy-1,3-bis-(benzyloxy) propane) is a preferred starting material for the hydrogenation step to give ganciclovir with the 2-amino group retained in protected form and one protected primary hydroxyl function. Suitable amino-protecting groups are lower alkanoyl groups with 2 to 4 carbon atoms, in particular the acetyl or propionyl group. Other suitable amino-protecting groups are the trityl or substituted trityl groups, such as the monomethoxytrityl group, and the 4,4'-dimethoxytrityl group. However, protection of the 2-amino group of the purine ring system is not required.

Suitable hydroxy-protecting groups are ether-forming groups that can be removed easily after completion of all other reaction steps. These hydroxy-protecting ether groups include the benzyl or the trityl group. These groups may be substituted in the phenyl ring. Other suitable hydroxy-protecting groups include allyl ether, tetrahydropyranyl, silyl, trialkylsilyl ethers which can be removed with hydrogen fluoride in a manner well known to those skilled in the art. Trityl groups can also be removed after the esterification step by treating the esterification product with an alkanoic acid, such as acetic or trifluoroacetic or hydrochloric acid. Benzyl groups will be removed with hydrogenation; allyl groups will be removed by isomerization to the vinyl ethers with rhodium or palladium catalysts followed by acidic aqueous hydrolysis.

The hydrogenation to remove one hydroxy-protecting group is preferably carried out by dissolving the protected ganciclovir in a solvent system that releases hydrogen in the presence of a catalyst such as a palladium compound, in particular palladium hydroxide, by transfer hydrogenation or other conventional hydrogenation procedures. Other suitable hydrogenation catalysts include hydrogenation catalysts in general such as Pd, Pd on carbon and homogeneous hydrogenation catalysts. The solvent system includes a lower alkanol such as methanol or ethanol and cyclohexene. Generally the reaction will be carried out at temperatures between room temperature and the reflux temperature of the solvent system, for example in refluxing ethanol and cyclohexene under an inert atmosphere and under exclusion of oxygen or air, preferably in a nitrogen atmosphere. The catalyst will be recovered by filtration. The filtrate can be reduced in volume by evaporation of excess solvent. The resulting crude reaction mixture generally includes unchanged starting material and 2-amino-protected ganciclovir with one aliphatic hydroxy group protected as the major products. The separation of these two products is usually performed by isolation procedures known in the art, often by chromatographic methods, preferably on silica gel, followed by elution with appropriate eluents such as mixtures of a lower alkanol with a halogenated lower alkane (preferably ethanol and dichloromethane) to give 2-amino-protected ganciclovir with one aliphatic hydroxy group protected.

Step II: Ganciclovir with a protected 2-amino group and one aliphatic hydroxy group protected is subjected to deprotection of the amino group. In this step if the amino-protecting group is a lower alkanoyl group, basic conditions (pH between 9 to 14) are employed to remove the protecting group. For example, N2-Acetyl-mono-O-benzyl-ganciclovir is treated with an alkaline reagent such as ammonium hydroxide, sodium or potassium carbonate or sodium or potassium hydroxide until the removal of the acetyl group is complete. In general, this reaction will be conducted in the presence of a suitable solvent such as a lower alkanol. Preferably the starting material is dissolved in methanol and a stoichiometric excess of ammonium hydroxide is added. The reaction temperature is kept between 0° to 50° C., preferably at room temperature. After the reaction is complete (which can be determined by TLC), another solvent such as ethyl ether may be added to give ganciclovir with one protected aliphatic hydroxy group which can be filtered off and isolated using conventional separation methods.

Step III: In this step an activated derivative of an amino-protected amino acid of the Formula IV is esterified with the protected ganciclovir derivative obtained in Step II. Suitable amino-protecting groups for the amino acid are the N-benzyloxycarbonyl group, the phthalyl group, the tertiary butyloxycarbonyl group and the N-(9-fluorenylmethoxycarbonyl) or "FMOC" group.

At least 1 equivalent of the protected amino acid and 1 equivalent of a suitable coupling agent or dehydrating agent, for example 1,3-dicyclohexylcarbodiimide or salts of such diimides with basic groups should be employed from the start. Other carbodiimides such as N,N'-carbonyldiimidazole may also be used. Further useful dehydrating agents are trifluoroacetic anhydride, mixed anhydrides, acid chlorides, 1-benzotriazolyloxytris(dimethylamino)-phosphonium hexafluorophosphate, PYBOP, 1-hydroxybenzotriazole, 1-hydroxy-4-azabenzotriazole, 1-hydroxy-7-azabenzotriazole, N-ethyl-N'-(3-(dimethylamino)propyl)-carbodiimide hydrochloride, 3-hydroxy-3,4-dihydro-4-oxo-1,2,3-benzotriazine, O-(benzotriazol-1-yl)-1,1,3,3-tetramethyluronium hexafluorophosphate, O-(7-azabenzotriazol-1-yl)-1,1,3,3-tetramethyluronium hexafluorophosphate, O-(7-azabenzotriazol-1-yl)-1,1,3,3-tetramethyluronium tetrafluoroborate, O-(1H-benzotriazol-1-yl)-1,1,3,3-bis(tetramethylene)uronium hexafluorophosphate or O-(7-azabenzotriazol-1-yl)-1,1,3,3-bis(tetramethylene)uronium hexafluorophosphate. A description of these coupling agents by L. A. Carpino can be found in *J. Am. Chem. Soc.* 1993, 115, p. 4397–4398. Also useful for this purpose are urethane-protected amino acid N-carboxy anhydrides which have been described by William D. Fuller et.al., *J. Am. Chem. Soc.* 1990, 112, 7414–7416, which is incorporated herein by reference. In summary, any other reagent that produces an anhydride or another activated derivative of the protected amino acid under mild conditions can be used as the coupling agent.

The amino-protected amino acid is dissolved in an inert solvent such as a halogenated lower alkane, preferably dichloromethane under an inert atmosphere, for example nitrogen, and the coupling agent is added (preferably 1,3-dicyclohexylcarbodiimide). The reaction mixture is stirred at temperatures between 0° and 50° C., preferably at about room temperature for about 10 to 24 hours. The reaction mixture is filtered and the reaction product (the anhydride of the protected amino acid) isolated. The resulting product is dissolved in a dry inert solvent such as dry DMF and placed under nitrogen. A solution of an equivalent amount of the product of Step II in an inert solvent is added to the above solution of the anhydride. The reaction is carried out between 0° and 50° C., preferably at about room temperature over 5 to 90 hours. The reaction product can be isolated and purified using conventional methods, such as chromatography. The product usually will contain unreacted N-protected amino acid which can be removed by treatment of a water-immiscible solution (organic phase) of the product with aqueous alkali such as sodium bicarbonate, sodium carbonate, brine and mixtures thereof. From the organic phase the ganciclovir amino acid ester with the protected aliphatic hydroxy group and the N-protected amino acid can be isolated and purified using conventional isolation and purification techniques.

Step IV (Final De-protection to Give the Product of Formula I): The two protecting groups of the product of Step III are removed by de-protection reactions, preferably in an acidic medium or solvent, most preferably by hydrogenation. De-protection under acidic conditions is preferred, as this will ensure that the amino group liberated in the de-protection reaction will be protonated, that is that the base of Formula I as it is formed in the de-protection reaction will be captured by an at least stoichiometric amount of acid present. Isolating the compound of Formula I as an acid addition salt will protect the desired stereoconfiguration of the compound of Formula I. Therefore, those examples given below that show the de-protection step (a) also show the concomitant salt formation step (b).

The de-protection is carried by dissolving the product of the esterification step in an inert solvent, preferably in an acidic solvent, using a hydrogenation catalyst, such as palladium on carbon, platinum, using elevated hydrogen pressure between 1 and 2000 psi, preferably 20 to 200 psi. The completion of the reaction can be monitored using conventional TLC analysis. The hydrogenation is continued until the conversion is complete, if required with addition of further hydrogenation catalyst. The catalyst is removed and washed. The combined filtrates from filtration and the washings are concentrated and lyophilized to isolate the desired ganciclovir amino acid ester of Formula I. The purification of the product and the isolation of a crystalline ester is carried out by recrystallization or other conventional purification techniques.

If the tertiary butyloxycarbonyl group is being used as amino-protecting group, its removal is effected with acid, such as HCl and isopropanol as a solvent or with trifluoroacetic acid neat.

Alternatively if the esterification step has been carried out with a trityl or substituted trityl-protected ganciclovir derivative such protecting groups can be removed by treatment with an aqueous alkanoic acid at temperatures between −20° C. and 100° C., for example, aqueous acetic acid.

Other Methods of Preparation [Steps (b), (c), (d), and (e)]

One of ordinary skill in the art will also recognize that a compound of Formula I may be prepared as an acid addition salt or as the corresponding free base. If prepared as an acid addition salt, the compound is converted to the free base by treatment with a suitable base such as ammonium hydroxide solution, sodium hydroxide, potassium hydroxide or the like. However, caution must be taken so that the compounds of Formula I are not racemized at higher pH. When converting a free base to an acid addition salt, the compound is reacted with a suitable organic or inorganic acid (described earlier). These reactions are effected by treatment with an at least stoichiometric amount of an appropriate acid (in case of the preparation of an acid addition salt) or base (in case of liberation of the free compound of Formula I). In the salt-forming step of this invention typically, the free base is dissolved in a polar solvent such as water or a lower alkanol (preferably isopropanol) and mixtures thereof and the acid is added in the required amount in water or in lower alkanol. The reaction temperature is usually kept at about 0° to 50° C., preferably at about room temperature. The corresponding salt precipitates spontaneously or can be brought out of the solution by the addition of a less polar solvent, removal of the solvent by evaporation or in a vacuum, or by cooling the solution.

Step (c) is carried out by esterifying ganciclovir (optionally with a protected 2-amino group) under controlled conditions with less than two equivalents, preferably 1.3 to 1.6 equivalents, of the compound of Formula IV under conditions described above for the preparation of the monoesters of Formula I, that is in the presence of a coupling agent at temperatures between 0° and 50° C.

The reaction conditions of condensation step (d) are described in European Patent Publication 187 297. The condensation step is the preferred route if the pure enantiomers of the compounds of the Formula I are to be prepared. The glycerol derivative of the Formula VI, such as 1,3-diacyloxy2-acyloxymethoxy-glycerol, is reacted with guanine or a substituted guanine derivative in an aprotic hydrocarbon solvent (such as benzene or toluene, or xylenes), or DMF, with a hexa-lower alkyl silazane (for example, hexamethylsilazane, hexaethylsilazane, or the like), and a catalyst at temperatures between 30° C. and reflux temperature.

The catalyst is a Lewis acid salt, such as a trialkylsilyl salt, for example, the sulfate or a trifluoroalkyl sulfonate, a chlorosilane, or ammonium sulfate and pyridine. For a more detailed disclosure of the reaction conditions for condensation step (e) see the disclosure of European Patent Publication 187 297 which is incorporated by reference herein. In general, the substituents $Y^1$ and $Y^2$ are selected in such a manner as to provide the compounds of Formula I. For example, $Y^1$ will be benzyloxy and $Y^2$ will be the amino-protected achiral amino acid acyl radical with a tertiary α-carbon atom described above or a group convertible to the achiral amino acid radical with a tertiary α-carbon atom described above.

Step (e), the partial hydrolysis of a bis-ester of the Formula III to the monoesters of Formula I is carried out under conditions which result in the preferential cleavage one only one amino acid acyl residue. To effect such partial hydrolysis, a salt of a compound of Formula III, preferably the bis acetate or hydrochloride is dissolved in de-ionized water, and partially neutralized with weak base, such as a dilute ammonium hydroxide solution. The mixture is then kept at room temperature for one to several days, preferably 48 to 72 hrs. The monoester can be separated from the bis ester by preparative chromatography under weak acidic conditions (pH 3 to 5, preferably pH 4). The solvent used for chromatographic separation is be removed and the desired salt of the compound of Formula I is isolated as a racemic mixture.

Alternatively, enzymatic hydrolysis with an esterase, such as porcine esterase or a peptidase, such as a carboxypeptidase can also be used to effect partial hydrolysis.

Isolation of Isomers

From Formula (I) it is apparent that the compounds of the invention may have at least one asymmetric carbon atom (chiral center). The compounds of Formula I which are monoesters have one asymmetric carbon atom in the aliphatic side chain. For the compounds of Formula I which have one asymmetric carbon atom, two enantiomeric forms exist, the (R)- and (S)-form as determined by the rules of Cahn et al.

A number of methods suitable for the resolution of enantiomers can be used, but the preferred methods depend on the preparation of diastereomeric compounds derived from the enantiomers. While the resolution can be achieved with covalent diastereomeric compounds derived from the compounds of Formula I and diastereomeric complexes, the preferred diastereomeric compounds are dissociable. In general, the covalent diastereomers are separated by chromatography but preferred are separation/resolution techniques depending on differences in solubility.

In a preferred method the compounds of Formula I with one asymmetric carbon atom are separated by the formation of crystalline diastereomeric salts between the racemic substrate (R, S) and an optically active acid. Examples of suitable resolving agents which may form dissociable salts with the enantiomers of Formula I are tartaric acid, o-nitroantranilic acid, mandelic acid, malic acid, 2-phenoxypropionic acid, hydratropic acid and 2-arylpropionic acids in general, or camphorsulfonic acid. Alternatively, selective crystallization, direct crystallization or chromatography can be used. Specifics of the resolution techniques applicable to the preparation of enantiomers of the Formula I are described in Jean Jacques, André Collet, Samuel H. Wilen, *Enantiomers, Racemates and Resolutions,* John Wiley & Sons, Inc. (1981), which is incorporated herein by reference.

Alternatively, the compounds of the invention may be prepared using optically active reactants. When chiral compounds of the Formula I are prepared the condensation step (e) will be the preferred method of synthesis.

The enantiomers of the compounds of Formula I may also be prepared by chromatographic methods, such as liquid chromatographic techniques on a chiral support.

The stereoconfiguration at the chiral center of the compounds of Formula I can be assigned by circular dichroism, preferably by Single Crystal X-Ray Analysis of a heavy atom derivative, or by correlation with material prepared by total synthesis from a single glycerol enantiomer of known configuration.

The Manufacture of Crystalline Compounds

The compounds of the invention can be produced in crystalline form. This is an advantage over the compounds disclosed in the prior art which have been described as non-crystalline materials. The advantage resides in the fact that pharmaceutical formulations can be more easily produced with a crystalline material. A crystalline material can be processed efficiently and is susceptible of being more reproducibly characterized than a non-crystalline material, and the quality of the crystalline materials of the invention can be much more readily ascertained than that of a non-crystalline material.

In order to produce crystalline materials it is preferred to produce a salt of the compound of Formula I. Preferred crystalline salts are the acetate and the hydrochloride salt. It is preferred to initiate crystallization of the salt by dissolving the hydrochloride or acetate salt in water and adding an organic solvent miscible with water such as methanol, ethanol, isopropanol, tetrahydrofuran or acetonitrile. Alternatively, the hydrochloride salt can be crystallized from an anhydrous lower alkanol solution, such as methanol or ethanol, by the addition of other organic solvents such as ethyl acetate, isopropanol, tetrahydrofuran or toluene.

The following preparations and examples are given to enable those skilled in the art to more clearly understand and to practice the present invention. They should not be considered as limiting the scope of the invention, but merely as being illustrative and representative thereof.

EXAMPLE 1

Preparation of N-Benzyloxycarbonyl-1-amino-cyclohexanecarboxylic acid

A. (Formula IV, wherein the two $R^2$ groups link together and form a cyclohexane ring with the a-carbon atom to which they are attached; $P^2$ is benzyloxycarbonyl)

1-Amino-cyclohexanecarboxylic acid, 5 g (35 mmol), was dissolved in ethanol (25 mL) and a solution of sodium hydroxide (1.68 g, 42 mmol) in water (25 mL) was added. The reaction mixture was cooled in an ice/water bath while benzyl chloroformate (5.96 mL, 42 mmol) in ethanol (20 mL) and 1N sodium hydroxide (42 mL, 42 mmol) were added simultaneously in a dropwise fashion. During this addition, the reaction mixture was stirred vigorously. Stirring was continued at 0°–2° C. for 2 hrs. and the reaction is stirred at room temperature over night. The reaction mixture was concentrated to dryness and the residue is partitioned between ethyl ether and water. The aqueous layer was acidified to pH 2 by the addition of 1N HCl and extracted with ethyl acetate. The ethyl acetate layer was washed with water followed by brine and dried over magnesium sulfate before evaporation to dryness. The resulting oil was crystallized from ethyl acetate hexane mixtures resulting in N-benzyloxycarbonyl-1-amino-cyclohexanecarboxylic acid, 6.85 g (24.7 mmol, 71%); mp 153.4°–153.9° C. Analysis Calcd. for $C_{15}H_{19}NO_4$ (277.325): C, 64.97; H, 6.91; N, 5.05. Found: C, 64.86; H, 6.91; N, 4.94.

B. (Formula IV, wherein the two $R^2$ groups link together and form a cycloalkane ring with 4–5 and 7–10 ring carbons with the α-carbon atom to which they are attached, or each $R^2$ group is methyl, ethyl, n-propyl, isopropyl, isobutyl, n-butyl, cyclopropyl, cyclobutyl or benzyl; $P^2$ is benzyloxy)

In a similar manner, using 1-amino-cyclobutanecarboxylic acid, 1-amino-cyclopentanecarboxylic acid, 1-amino-cycloheptane-carboxylic acid, 1-amino-cyclooctanecarboxylic acid, 1-amino-cyclononanecarboxylic acid, 1-amino-cyclodecanecarboxylic acid, 2-amino-2-methylpropionic acid, 2-amino-2-ethylbutyric acid, 2-amino-2-n-propylvaleric acid, 2-amino-2-isopropyl-3-methylbutyric acid, 2-amino-2-isobutyl-4-methylvaleric acid, 2-amino-2-n-butylhexanoic acid, 2-amino-2,2-biscyclopropylacetic acid, 2-amino-2,2-biscyclobutylacetic acid or 2-amino-2,2-bisbenzylacetic acid instead of 1-amino-cyclohexanecarboxylic acid, the following starting materials are prepared:

N-benzyloxycarbonyl-1-amino-cyclobutanecarboxylic acid;

N-benzyloxycarbonyl-1-amino-cyclopentanecarboxylic acid;

N-benzyloxycarbonyl-1-amino-cycloheptanecarboxylic acid;

N-benzyloxycarbonyl-1-amino-cyclooctanecarboxylic acid;

N-benzyloxycarbonyl-1-amino-cyclononanecarboxylic acid;

N-benzyloxycarbonyl-1-amino-cyclodecanecarboxylic acid;

N-benzyloxycarbonyl-2-amino-2-methylpropionic acid;

N-benzyloxycarbonyl-2-amino-2-ethylbutyric acid;

N-benzyloxycarbonyl-2-amino-2-n-propylvaleric acid;

N-benzyloxycarbonyl-2-amino-2-isopropyl-3-methylbutyric acid;

N-benzyloxycarbonyl-2-amino-2-isobutyl-4-methylvaleric acid;

N-benzyloxycarbonyl-2-amino-2-n-butylhexanoic acid;

N-benzyloxycarbonyl-2-amino-2,2-biscyclopropylacetic acid;

N-benzyloxycarbonyl-2-amino-2,2-biscyclobutylacetic acid; and

N-benzyloxycarbonyl-2-amino-2,2-bisbenzylacetic acid.

C. (Formula IV, wherein the two $R^2$ groups link together and form a cycloalkane ring with 4–10 ring carbons with the α-carbon atom to which they are attached, or each $R^2$ group is methyl, ethyl, n-propyl, isopropyl, isobutyl, n-butyl, cyclopropyl, cyclobutyl or benzyl; $P^2$ is benzyloxy); $P^2$ is t-butyloxycarbonyl)

Using tertiary butylchlorocarbonate (t-BOC) as a reagent instead of benzyl chloroformate in a similar manner the following starting materials are be prepared:

N-t-BOC-1-amino-cyclobutanecarboxylic acid;

N-t-BOC-1-amino-cyclopentanecarboxylic acid;

N-t-BOC-1-amino-cyclohexanecarboxylic acid;

N-t-BOC-1-amino-cycloheptanecarboxylic acid;

N-t-BOC-1-amino-cyclooctanecarboxylic acid;

N-t-BOC-1-amino-cyclononanecarboxylic acid;

N-t-BOC-1-amino-cyclodecanecarboxylic acid;

N-t-BOC-2-amino-2-methylpropionic acid;

N-t-BOC-2-amino-2-ethylbutyric acid;

N-t-BOC-2-amino-2-n-propylvaleric acid;

N-t-BOC-2-amino-2-isopropyl-3-methylbutyric acid;

N-t-BOC-2-amino-2-isobutyl-4-methylvaleric acid;

N-t-BOC-2-amino-2-n-butylhexanoic acid;

N-t-BOC-2-amino-2,2-biscyclopropylacetic acid;

N-t-BOC-2-amino-2,2-biscyclobutylacetic acid; and

N-t-BOC-2-amino-2,2-bisbenzylacetic acid.

EXAMPLE 2

Preparation of
2-(2-Amino-1,6-dihydro-6-oxo-purin-9-yl)methoxy-1-benzyloxypropan-3-ol A. N2-Acetyl-2-(2-amino-1,6-dihydro-6-oxo-purin-9-yl) methoxy-1,3-bis(benzyloxy)-propane, 54.2 g (114 mmol) was dissolved in refluxing ethanol (815 mL) and cyclohexene (610 mL) was added under a nitrogen atmosphere. A slurry of palladium hydroxide (16 g) in ethanol (50 mL) was added to the reaction mixture and the mixture refluxed under nitrogen for 1.5 hrs. The hot mixture was filtered through Celite and the filtrate concentrated on a rotary evaporator. The resulting crude reaction mixture was chromatographed on silica gel. Elution with 8% methanol/92% dichloromethane followed by 10% methanol/90% dichloromethane resulted in N2-Acetyl-2-(2-amino-1,6-dihydro-6-oxo-purin-9-yl)methoxy-1,3-bis(benzyloxy)propane (unchanged starting material) (18.6 g, 16%) and N2-acetyl-2-(2-amino-1,6-dihydro-6-oxo-purin-9-yl)methoxy-1-benzyloxy-propan-3-ol, (17.6 g, 40%).

B. N2-Acetyl-2-(2-amino-1,6-dihydro-6-oxo-purin-9-yl) methoxy-1-benzyloxy-propan-3-ol, 21.9 g (56.5 mmol), was dissolved in methanol (200 mL) and ammonium hydroxide (101 mL) was added. The mixture was stirred over night at room temperature. Ethyl ether (400 mL) was added to the white slurry and the mixture was filtered. The precipitate was washed consecutively with ethyl ether (100 mL), water (100 mL) and ethyl ether (100 mL) and dried under high vacuum over night resulting in 15.9 g (46.13 mmol, 82%) of 2-(2-amino-1,6-dihydro-6-oxo-purin-9-yl) methoxy-1-benzyloxy-propan-3-ol. Evaporation of the filtrate and suspension of the resulting precipitate in ethyl ether (200 mL) followed by filtration and drying under high vacuum resulted in an additional 2.3 g (6.7 mmol, 12%) of the product.

Analysis Calcd. for $C_{16}H_{19}N_5O_4$ (345.36): C, 55.65; H, 5.55; N, 20.28. Found: C, 55.25; H, 5.60; N, 20.12.

EXAMPLE 3

Preparation of
(S)-2-(2-Amino-1,6-dihydro-6-oxo-purin-9-yl) methoxy-3-benzyloxy-propan-1-ol A. (R)-(1-Chloro-2-acetoxymethoxy-3-benzyloxy)propane HCl gas (dried by passing through concentrated $H_2SO_4$) was bubbled into a stirred mixture of (S)-(+)-benzyloxymethyloxirane (500 mg, 3.06 mmol) and paraformaldehyde (201 mg, 6.71 mmol) in dichloromethane (8 mL) at 0° C. until all the solid dissolved (ca. 45 min). The resulting solution was stored at 0° C. for 16 hours. After drying with magnesium sulfate, the solvent was evaporated to provide the chloromethyl ether intermediate (R)-(1-chloro-2-chloromethoxy-3-benzyloxy)propane. This intermediate was dissolved in acetone (3 mL) and added dropwise to a mixture of potassium acetate (2.1 g, 21.4 mmol) in acetone (7 mL). The mixture was stirred at ambient temperature for 16 hours. The solid was filtered off and the filtrate concentrated. The residue was taken up in 20 mL of toluene and the washed with saturated sodium bicarbonate solution (10 mL) and water (2×20 mL). The organic layer was dried over sodium sulfate. After filtration, the filtrate was concentrated and the residue purified by flash chromatography over silica gel (hexanes/ethyl acetate=7/1) to provide (R)-(1-chloro-2-acetoxymethoxy-3-benzyloxy)propane (810 mg, 2.97 mmol) as a colorless oil in 97% yield (the isomeric ratio was 12:1).

B. (R) 2-(2-Amino-1,6-dihydro-6-oxo-purin-9-yl) methoxy-1-chloro-3-benzyloxy-propane A solution of persilylated guanine (1.09 g, 2.95 mmol) in DMF (3.2 mL) was added to 810 mg of (R)-(1-chloro-2-acetoxymethoxy-3-benzyloxy)propane. The solution was stirred at 130° C. for 1 hour before trimethylsilyl trifluoromethanesulfonate was introduced. Stirring was continued at the same temperature for 4 hours. The mixture was cooled to room temperature and partitioned between water and ethyl acetate. The aqueous layer was extracted exhaustively with ethyl acetate. The combined organic layer was dried over magnesium sulfate, filtered and concentrated. The residue was purified by chromatography over silica gel to provide (R)-2-(2-amino-1,6-dihydro-6-oxo-purin-9-yl)methoxy-1-chloro-3-benzyloxypropane along with its N-7 isomer. The ratio of N-9 to N-7 isomer was about 2.3:1.

C. (R)-2-(2-amino-1,6-dihydro-6-oxo-purin-9-yl) methoxy-1-acetoxy-3-benzyloxy-propane A mixture of the product from the previous step, potassium acetate (large excess) and DMF was heated to reflux for 5 hours. The resulting brown mixture was cooled to room temperature and filtered through a plug of Celite. The filter bed was rinsed with methanol. The filtrate was evaporated and residual DMF removed in vacuo. The crude product was purified by flash chromatography over silica gel ($CH_2Cl_2$-methanol: 10:1) to provide (R)-2-(2-amino-1,6-dihydro-6-oxo-purin-9-yl)methoxy-1-acetoxy-3-benzyloxy-propane as a pale yellow solid.

D. (S) 2-(2-Amino-1,6-dihydro-6-oxo-purin-9-yl) methoxy-1-benzyloxy-propan-3-ol

A mixture of (R)-2-(2-amino-1,6-dihydro-6-oxo-purin-9-yl)methoxy-1-acetoxy-3-benzyloxy-propane in 30% ammonia/methanol (1:2) was stirred at ambient temperature for 18 hours. The solvent was evaporated and the residue was triturated with a small amount of methanol. The pale yellow solid was collected to give (S)-2-(2-Amino-1,6-dihydro-6-oxo-purin-9-yl)methoxy-1-benzyloxy-propan-3-ol. The mother liquor was concentrated and the residue recrystallized from hot methanol to give a second crop of the product.

EXAMPLE 4

Preparation of 2-(2-Amino-1,6-dihydro-6-oxo-purin-9-yl)methoxy-3-hydroxy-1-propanyl (1-amino-cyclohexane-carboxylate)

(Formula I: X is hydroxy; the two $R^2$ groups together with the α-carbon to which they are attached form a cyclohexyl ring)

A. N-Benzyloxycarbonyl-1-amino-cyclohexanecarboxylic acid, 6.02 g (21.7 mmol, 1.5 equivalents) was dissolved in dichloromethane (240 mL) under nitrogen and 1,3-dicyclohexylcarbodiimide, 3.88 g (18.8 mmol, 1.3 equivalents) was added under stirring. The reaction mixture was stirred at room temperature for 6.5 hrs. The mixture was filtered and the filtrate was concentrated on a rotary evaporator. The resulting white foam was dissolved in dry DMF (90 mL) and placed under nitrogen. 2-(2-Amino-1,6-dihydro-6-oxo-purin-9-yl)methoxy-1-benzyloxy-propan-3-ol, 5 g (14.5 mmol), was dissolved in dry DMF (90 mL) and added to the above solution of the anhydride in DMF. Following the addition of 4-dimethylamino-pyridine, 0.27 g (2.2 mmol, 0.15 equivalents), the reaction mixture was stirred over night at room temperature. TLC analysis indicated that the reaction was incomplete.

N-Benzyloxycarbonyl-1-amino-cyclohexanecarboxylic acid, 1.2 g (4.3 mmol, 0.3 equivalents), and 1,3-dicyclohexylcarbodiimide, 0.9 g (4.3 mmol, 0.3 equivalents), were added and the reaction mixture was stirred for 3 days at room temperature. The mixture was filtered and the filtrate evaporated to dryness. Chromatography on silica gel with the solvent system 7.5% methanol/92.5% dichloromethane results in impure product, 7.6 g. Rechromatography on silica gel with the solvent system made from dichloromethane (2 L), acetone (2 L) and acetic acid (30 mL) gives a crude product. This product was dissolved in chloroform (150 mL) and washed with saturated sodium bicarbonate (300 mL) followed by water (200 mL) and brine (200 mL) to remove the remaining N-benzyloxycarbonyl-1-amino-cyclohexanecarboxylic acid. The organic phase was dried over magnesium sulfate and evaporated to dryness to give 6.49 g (10.7 mmol, 74%) of the product 2-(2-amino-1,6-dihydro-6-oxo-purin-9-yl)methoxy-1-benzyloxy-propan-3-ol (N-benzyloxycarbonyl-1-amino-cyclohexanecarboxylate) as a white foam.

The reaction was completed by using 2 equivalents of the amino acid and 1 equivalent of 1,3-dicyclohexyl-carbodiimide from the start.

B. Preparation of 2-(2-Amino-1,6-dihydro-6-oxo-purin-9-yl)methoxy3-hydroxy-1-propanyl (1-amino-cyclohexanecarboxylate) acetate The benzyl ether of the previous step, 6.16 g (10.19 mmol), was dissolved in glacial acetic acid (280 mL). Palladium on carbon, 3 g, was added and the mixture was hydrogenated on a Parr shaker at 40 psi over night. TLC analysis indicated a conversion of approximately 90%. The mixture was hydrogenated for an additional 5 hours under the same conditions. Conversion was still not complete. Palladium on carbon, 3 g, was added and hydrogenation continued over night. The reaction mixture was filtered through a pad of Celite and the charcoal catalyst was washed with acetic acid (200 mL) followed by water (150 mL). The filtrate was filtered through a glass frit (medium pore size) and concentrated to a volume of about 75 mL. Water, 500 mL, was added and mixture was divided into four equal parts and each part was lyophilized (1 L round bottom flask) to a white lyophilized powder resulting in 2-(2-amino-1,6-dihydro-6-oxo-purin-9-yl)methoxy-3-hydroxy-1-propanyl (1-amino-cyclohexanecarboxylate) acetate, 3.1 g (6.6 mmol, 64%): mp 141.5°–151.5° C. 2. Combustion Analysis: $C_{16}H_{24}N_6O_5+CH_3COOH+1.75 H_2O$ (471.98). Calcd for C, 45.81; H, 6.72; N, 17.81. Found: C, 45.82; H, 6.38; N, 17.93.

C. Preparation of (R)-2-(2-Amino-1,6-dihydro-6-oxo-purin-9-yl)methoxy-3-benzyloxy-1-propanyl (N-benzyloxycarbonyl-1-amino-cyclohexanecarboxylate)

To a solution of N-benzyloxycarbonyl-1-aminocyclohexane-carboxylate (2.41 g, 8.7 mmol, 2 equivalents) in anhydrous dimethylformamide (12 mL) at 0° C. under nitrogen was added 1,3-di-cyclohexylcarbodiimide (1.79 g, 8.7 mmol, 2 equivalents) followed by 4-dimethylaminopyridine (53 mg, 0.44 mmol). A solution of (S)-2-(2-amino-1,6-dihydro-6-oxo-purin-9-yl)methoxy-3-benzyloxy-propan-1-ol (1.5 g, 4.35 mmol) in dimethylformamide (20 mL) was added dropwise under stirring at 0° C. Stirring was continued at room temperature for 20 hrs. The white solid was filtered off and rinsed with dichloromethane. The filtrate was evaporated to dryness under vacuum, dichloromethane was added to the residue and the mixture was filtered again to remove dicyclohexyl urea. The filtrate was chromatographed on a silica gel column using a solvent system of dichloromethane/methanol=15:1 for elution. 1.9 g (3.15 mmol, 73%) of (R)-2-(2-amino-1,6-dihydro-6-oxo-purin-9-yl)methoxy-3-benzyloxy-1-propanyl (N-benzyloxycarbonyl)-1-aminocyclohexanecarboxylate was obtained. m.p 116°–118° C. (from ethylacetate/ether crystallization); $[\alpha]_D$= –6.79° (c=0.75, CHCl$_3$).

D. Preparation of (R,S)-2-(2-Amino-1,6-dihydro-6-oxo-purin-9-yl)methoxy-3-hydroxy-1-propanyl (1-amino-cyclohexanecarboxylate) acetate The benzyl ether of the previous step, 1.58 g (2.55 mmol), was dissolved in glacial acetic acid (70 mL). Palladium on carbon, 1 g, was added and the mixture was hydrogenated on a Parr shaker at 40 psi over night. TLC analysis indicated a conversion of approximately 90%. The mixture was hydrogenated for an additional 5 hours under the same conditions. The conversion was still not complete. Palladium on carbon, 1 g, was added and the hydrogenation continued over night. The reaction mixture was filtered through a pad of Celite and the charcoal catalyst was washed with acetic acid (50 mL) followed by water (40 mL). The filtrate was filtered through a glass frit (medium pore size) and concentrated to a volume of about 20 mL. Water, 125 mL, was added and mixture was divided into four equal parts and each part was lyophilized to a white lyophilized powder resulting in (R,S)-2-(2-amino-1,6-dihydro-6-oxo-purin-9-yl)methoxy-3-hydroxy-1-propanyl (1-amino-cyclohexane-carboxylate) acetate, 0.75 g (3.25 mmol, 64%), showing that racemization occurred in the hydrogenation step. Combustion Analysis: $C_{16}H_{24}N_6O_5$+ $CH_3COOH$+1.75 $H_2O$ (471.98). Calcd for C, 45.81; H, 6.72; N, 17.81. Found: C, 45.82; H, 6.38; N, 17.93.

E. Preparation of (R)-2-(2-Amino-1,6-dihydro-6-oxo-purin-9-yl)methoxy-3-hydroxy-1-propanyl (1-aminocyclohexanecarboxylate) hydrochloride salt (R)-2-(2-amino-1,6-dihydro-6-oxo-purin-9-yl)methoxy-3-benzyloxy-1-propanyl (N-benzyloxycarbonyl)-1-aminocyclohexane-carboxylate (0.8 g, 1.3 mmol) is dissolved in methanol (45 mL) and concentrated hydrochloric acid (0.118 mL, 1.3 mmol) is added. The mixture is placed under nitrogen and 10% palladium on carbon (250 mg) is added. The mixture is hydrogenated in a Parr shaker under hydrogen (50 psi of pressure) for 5 hours. The mixture is filtered through a pad of Celite and the residue washed with methanol (50 mL). Evaporation of the combined filtrate and washings under reduced pressure, followed by lyophilization from water (80 mL), yields the title compound (515 mg, 95%).

EXAMPLE 5

(Formula I: X is hydroxy; the two $R^2$ groups together with the α-carbon atom to which they are attached form a 4–10 ring carbon containing cycloalkyl ring; or each $R^2$ group is methyl, ethyl n-propyl, isopropyl, isobutyl, n-butyl, cyclopropyl, cyclobutyl or benzyl)

Using the procedures of Examples 1 and 2 and procedures similar to those of Example 3 but using 1-amino-cyclobutane-carboxylic acid, 1-amino-cyclopentanecarboxylic acid, 1-amino-cycloheptanecarboxylic acid, 1-amino-cyclooctanecarboxylic acid, 1-amino-cyclononanecarboxylic acid, 1-amino-cyclodecanecarboxylic acid, 2-amino-2-methylpropionic acid, 2-amino-2-ethylbutyric acid, 2-amino-2-n-propylvaleric acid, 2-amino-2-isopropyl-3-methylbutyric acid, 2-amino-2-isobutyl-4-methylvaleric acid, 2-amino-2-n-butyl-hexanoic acid, 2-amino-2,2-biscyclopropylacetic acid, 2-amino-2,2-biscyclobutylacetic acid or 2-amino-2,2-bisbenzylacetic acid instead of 1-amino-cyclohexanecarboxylic acid, the following compounds of Formula I are prepared:

2-(2-amino-1,6-dihydro-6-oxo-purin-9-yl)methoxy-3-hydroxy-1-propanyl (1-amino-cyclobutanecarboxylate) and its acetate: C14H20N6O5 . C2H4O2 (Mw: 352+60): MS (EI): 353 (M+);

2-(2-Amino-1,6-dihydro-6-oxo-purin-9-yl)methoxy-3-hydroxy-1-propanyl (1-amino-cyclopentanecarboxylate) and its acetate. C15H22N6O5 . C2H4O2 (Mw: 366+60): MS (LIMS): 367 (M+H)$^+$;

2-(2-Amino-1,6-dihydro-6-oxo-purin-9-yl)methoxy-3-hydroxy-1-propanyl (1-amino-cycloheptanecarboxylate) and its acetate. Molecular weight: C17H26N6O5 . C2H4O2 (Mw: 394+60); MS (EI): 394 (M+);

2-(2-Amino-1,6-dihydro-6-oxo-purin-9-yl)methoxy-3-hydroxy-1-propanyl (1-amino-cyclooctanecarboxylate) and its hydrochloride;

2-(2-Amino-1,6-dihydro-6-oxo-purin-9-yl)methoxy-3-hydroxy-1-propanyl (1-amino-cyclononanecarboxylate) and its hydrochloride;

2-(2-Amino-1,6-dihydro-6-oxo-purin-9-yl)methoxy-3-hydroxy-1-propanyl (1-amino-cyclodecanecarboxylate) and its hydrochloride;

2-(2-amino-1,6-dihydro-6-oxo-purin-9-yl)methoxy-3-hydroxy-1-propanyl (2-amino-2-methylpropionate) and its acetate [Yield of esterification: 70.6% of theory. Yield of hydrogenation: 100% of theory. C13H20N6O5 . C2H4O2. (Mw: 340+60): MS (LSIMS, glycerol matrix): 341 (M+H)$^+$];

2-(2-amino-1,6-dihydro-6-oxo-purin-9-yl)methoxy-3-hydroxy-1-propanyl (2-amino-2-ethylbutyrate) and its hydrochloride;

2-(2-amino-1,6-dihydro-6-oxo-purin-9-yl)methoxy-3-hydroxy-1-propanyl (2-amino-2-n-propylvalerate) and its hydrochloride;

2-(2-amino-1,6-dihydro-6-oxo-purin-9-yl)methoxy-3-hydroxy-1-propanyl (2-amino-2-isopropyl-3-methylbutyrate) and its hydrochloride;

2-(2-amino-1,6-dihydro-6-oxo-purin-9-yl)methoxy-3-hydroxy-1-propanyl (2-amino-2-isobutyl-4-methylvalerate) and its hydrochloride;

2-(2-amino-1,6-dihydro-6-oxo-purin-9-yl)methoxy-3-hydroxy-1-propanyl (2-amino-2-n-butylhexanoate) and its hydrochloride;

2-(2-amino-1,6-dihydro-6-oxo-purin-9-yl)methoxy-3-hydroxy-1-propanyl (2-amino-2,2-biscyclopropylacetate) and its hydrochloride;

2-(2-amino-1,6-dihydro-6-oxo-purin-9-yl)methoxy-3-hydroxy-1-propanyl (2-amino-2,2-biscyclobutylacetate) and its hydrochloride; and 2-(2-amino-1,6-dihydro-6-oxo-purin-9-yl)methoxy-3-hydroxy-1-propanyl (2-amino-2,2-bisbenzylacetate) and its hydrochloride.

EXAMPLE 6

Preparation of
2-(2-Amino-1,6-dihydro-6-oxo-purin-9-yl)methoxy-1,3-propanediyl bis
(1-amino-cyclohexanecarboxylate)

(Formula III: X is hydroxy; the two $R^2$ groups together with the α-carbon to which they are attached form a cyclohexyl ring)

A. 2-(2-Amino-1,6-dihydro-6-oxo-purin-9-yl)methoxy-1,3-propanediyl bis (N-benzyloxycarbonyl-1-amino-cyclohexane-carboxylate)

2-(2-Amino-1,6-dihydro-6-oxo-purin-9-yl)methoxy-1,3-propanediol, 2.0 g (7.8 mmol), and N-benzyloxycarbonyl-1-amino-cyclohexanecarboxylic acid, 8.68 g (31.2 mmol), were suspended in dry DMF (100 mL) under a nitrogen atmosphere. 4-Dimethylamino-pyridine, 381 mg (3.12 mmol), followed by 1,3-dicyclohexyl-carbodiimide, 6.43 g (31.2 mmol) were added under stirring. The mixture was stirred at room temperature for two days. The solvent was removed under reduced pressure and the residue was chromatographed on a silica gel column using dichloromethane containing 5% methanol as the eluant to provide 2-(2-amino-1,6-dihydro-6-oxo-purin-9-yl)methoxy-1,3-propanediyl bis (N-benzyloxycarbonyl-1-amino-cyclohexanecarboxylate) as a white solid.

B. 2-(2-Amino-1,6-dihydro-6-oxo-purin-9-yl)methoxy-1, 3-propanediyl bis (1-amino-cyclohexane carboxylate)

To a solution of 2-(2-amino-1,6-dihydro-6-oxo-purin-9-yl)methoxy-1,3-propanediyl bis (N-benzyloxycarbonyl-1-amino-cyclohexanecarboxylate), 2.0 g (2.58 mmol) in glacial acetic acid (30 mL) was added palladium on carbon (10%, 0.5 g) and the mixture was hydrogenated under 1 atmosphere hydrogen overnight at room temperature. The mixture was filtered through Celite and the filtrate concentrated under reduced pressure to a thick oil. Water was added to the residue and the mixture was lyophilized to give 2-(2-amino-1,6-dihydro-6-oxo-purin-9-yl)methoxy-1,3-propanediyl bis (1-amino-cyclohexanecarboxylate) as an acetate as a white solid. Mass spectrum: $MA^+$ 506; Mw 505. Elemental Analysis: $C_{29}H_{47}O_{12}N_7 \cdot 1HOAc \cdot 1H_2O$. Calc.: C 49.49; H 7.02; N 13.93. Found: C 49.32; H 6.97; N 13.89.

C. 2-(2-Amino-1,6-dihydro-6-oxo-purin-9-yl)methoxy-1, 3-propanediyl bis (1-amino-cyclopentanecarboxylate) and other bis (1-amino-cycloalkylcarboxylates)

(Formula III: X is hydroxy; the two $R^2$ groups together with the α-carbon atom to which they are attached form a cyclopentyl ring)

Using the method of Paragraphs A and B of this example the following compounds were prepared:

2-(2-Amino-1,6-dihydro-6-oxo-purin-9-yl)methoxy-1,3-propanediyl bis (1-amino-cyclopentanecarboxylate) bis acetate: $C_{21}H_{31}N_7O_6 \cdot 2 (C_2H_4O_2)$ (Mw: 477+120): MS (LIMS): 478 $(M+H)^+$;

2-(2-Amino-1,6-dihydro-6-oxo-purin-9-yl)methoxy-1,3-propanediyl bis (1-amino-cycloheptanecarboxylate) bis-acetate. $C_{25}H_{39}N_7O_6 \cdot 2(C_2H_4O_2)$ (Mw: 533+120). MS (LSIMS, glycerol matrix): 534 $(M+H)^+$; and 2-(2-Amino-1,6-dihydro-6-oxo-purin-9-yl)methoxy-1,3-propanediyl bis (1-amino-cyclobutanecarboxylate) bis-acetate. $C_{19}H_{27}N_7O_6 \cdot 2(C_2H_4O_2)$ (Mw: 449+120): MS (LSIMS): 450 $(M+H)^+$.

EXAMPLE 7

2-((2-Amino-1,6-dihydro-6-oxo-9H-purin-9-yl)methoxy)-3-hydroxy-1-propanyl
(1-amino-cyclohexane-carboxylate)acetate 2-((2-Amino-1,6-dihydro-6-oxo-purin-9-yl)methoxy)-1, 3-propanediyl bis-(1-amino-cyclohexane-carboxylate) tris acetate, 98 mg (lyophilized sample contained 3.0 equivalents of acetic acid by NMR), 0.143 mmol (=a total of 0.43 mmol of acetic acid) is dissolved in de-ionized water, 0.4 mL, and 38 µL of a 0.015M ammonium hydroxide solution (=0.57 mmol) is added. The mixture is left at room temperature for 7 hrs., the vial is placed in a oil bath maintained at 48°–50° C. and left in the oil bath for 22 hrs. The sample is injected in two equal lots onto a preparative reverse phase HPLC column (YMC-Pack, ODS-AM DM-33-5, 20×250 mm; YMC Inc.). Separation is achieved with a solvent system of 15% methanol/85% 0.1M ammonium acetate buffered to pH 4 with acetic acid, flow rate: 9.5 mL/min and the detector set to 256 nm. The peak representing the mono ester is collected. The solvent is removed under high vacuum to about 2 mL and the residue is lyophilized three times from water containing acetic acid (0.1%) to remove the buffer. Excess acetic acid is then removed by drying at room temperature under high vacuum for 42 hrs. 30 mg (0.068 mmol=48%) of 2-(2-amino-1,6-dihydro-6-oxo purin-9-yl)methoxy)-3-hydroxy-1-propanyl (1-amino-cyclohexane-carboxylate) acetate, identical by HPLC and NMR with the product of Example 4B, is obtained.

EXAMPLE 8

Determination of Oral Absorption (Bioavailability) in the Rat

The following assay was used to determine the oral absorption (oral bioavailability) of the compounds of Formula I and of ganciclovir amino acid esters, other ganciclovir esters and ethers examined for comparative purposes.

To measure the oral bioavailability of a compound first the plasma level of the compound in male rats was determined after a single oral (p.o.) dose of the compound. To measure the oral bioavailability of a pro-drug, first the plasma level of the active compound, in this case ganciclovir, was determined in male rats after a single po dose of the pro-drug. Then the plasma level of the active compound, ganciclovir, is determined in male rats after a single intravenous (iv) dose of the compound. For ganciclovir the single dose in each case, po and iv, is 10 mg/kg; for a prodrug ester the single dose in each case, oral and iv, is a dose equimolar to 10 mg/kg of ganciclovir. From the two measurements following p.o. and iv administration, the oral bioavailability of a compound was calculated by dividing the total area under the concentration vs. time curve following p.o. administration by the total area under the concentration vs. time curve following iv administration, appropriately corrected for dose, according to the equation:

$$F_{(p.o.)}(\%) = [AUC_{(p.o.)}/AUC_{(i.v.)}] \times [Dose_{(i.v.)}/Dose_{(p.o.)}] \times 100$$

The AUC (total area under the curve) values were calculated over the entire time range which was analyzed from 0–24 hr.

The dose vehicle for oral and intravenous dosing consisted of normal saline containing 2% of acetic acid. In both cases the compound concentration was equivalent to 4.0 mg/mL ganciclovir with a dose rate equivalent to 10 mg/kg (2.5 mL/kg) of ganciclovir. A 200 gm rat received 0.5 mL of the oral drug solution by garage or via injection into the tail vein.

The rats were acclimatized to the laboratory environment for three days and fasted overnight before start of the experiment and until 4 hours after dosing. Blood was collected from 4 rats at each of the following times: 0 min (pre-dose), 5 min (iv only), 15 min, 30 min, 1 hr, 2 hr, 3 hr, 5 hr, 7 hr, 10 hr and 24 hr. The blood was immediately centrifuged to obtain the plasma and the plasma frozen at −20° C. until analysis.

Assay of Ganciclovir in Plasma

Aliquots of plasma (0.50 mL) were mixed with 0.020 mL of internal standard (acyclovir, 15 µg/mL in 10% methanol/water) and 3.0 mL of acetonitrile. the mixture was vortexed and the resulting precipitate was removed by centrifugation (4,000 g, 10 min). The supernatant was evaporated to dryness under nitrogen and reconstituted in 200 µL of HPLC mobile phase. Aliquots (0.05 mL) were analyzed by HPLC using a Keystone Hypersil BDS, 250×4.6 mm C 18 column. The mobile phase contained 2% acetonitrile in 30 mM sodium phosphate buffer containing 5 mM heptane sulfonic acid, pH 2.0 and was pumped at 1.0 mL/min. Ganciclovir and internal standard were detected and measured by UV absorbance at 254 nm.

When tested in this assay, the monoesters of the Formula I exhibit a bioavailability which is substantially greater than that of ganciclovir and the bis esters of Formula III exhibit a bioavailability greater than that of ganciclovir.

EXAMPLE 9

Determination of Oral Absorption (Bioavailability) in the Cynomolgus Monkey

The following assay was used to determine the oral absorption (oral bioavailability) of the compounds of Formula I in the Cynomolgus Monkey.

Animals, Dosing and Sample Collection

Male cynomolgus monkeys weighing 5 to 7 kilos were used. The animals were fed monkey chow, fruit and water and maintained on a 12 hour light cycle. The compounds of Formula I were formulated at a concentration equimolar to a 10 mg/mL solution of ganciclovir in saline. The oral formulation was administered by garage at a rate of 1.0 mL/kg for a final dose equimolar to a 10 mg/kg dose of ganciclovir. The iv formulation of ganciclovir was formulated in saline containing 0.2% HCl at a concentration of 20 mg/mL and administered at a rate of 0.5 mL/kg.

The animals were fasted beginning the evening prior to dosing and until 4 hr after dosing. Blood samples were taken from each monkey at 0 (predose), 5 min (iv only), 15 min, 30 min, 1 hr, 2 hr, 3 hr, 5 hr, 7 hr, 10 hr and 24 hr after dosing. The blood samples were collected in heparinized syringes and the plasma was immediately isolated by centrifugation and frozen at −20° C. until analysis.

Assay of Ganciclovir in Plasma

Aliquots of plasma (0.50 mL) were mixed with 0.020 mL of internal standard (acyclovir, 15 µg/mL in 10% methanol/water) and 3.0 mL of acetonitrile. the mixture was vortexed and the resulting precipitate was removed by centrifugation (4,000 g, 10 min). The supernatant was evaporated to dryness under nitrogen and reconstituted in 200 µL of HPLC mobile phase. Aliquots (0.05 mL) were analyzed by HPLC using a Keystone Hypersil BDS, 250×4.6 mm C 18 column. The mobile phase contained 2% acetonitrile in 30 mM sodium phosphate buffer containing 5 mM heptane sulfonic acid, pH 2.0 and was pumped at 1.0 mL/min. Ganciclovir and internal standard were detected and measured by UV absorbance at 254 nm.

The bioavailability (F) is calculated according to the equation given in Example 8.

When tested in this assay, the monoesters of the Formula I exhibit a bioavailability which is substantially greater than that of ganciclovir.

EXAMPLE 10

Pharmaceutical Formulations

This example illustrates the preparation of representative pharmaceutical formulations for oral administration containing a ganciclovir monoester of Formula I, e.g., 2-(2-amino-1,6-dihydro-6-oxo-purin-9-yl)methoxy-3-hydroxy-1-propanyl (1-amino-cyclohexane-carboxylate) acetate.

The following ganciclovir monoester capsules contain as excipients povidone, a binder; corn starch, a disintegrant; and stearic acid, a lubricant and glidant; which are filled into a two piece hard gelatin capsule shell. Water is the granulating liquid, and is essentially removed during processing.

Quantitative Composition of Ganciclovir Monoester Capsules
(One Capsule Three Times Per Day)

| Ingredients | Weight Per Capsule (mg) | % W/W |
|---|---|---|
| Ganciclovir monoester hydrochloride | 390.00 | 92.75 |
| Povidone | 12.61 | 3.00 |
| Corn starch | 16.81 | 4.00 |
| Stearic acid[1] | 1.05 | 0.25 |
| Water[2] | | |
| Total fill weight (theoretical)[3] | 420.47 | 100.00 |

The powder blend is filled into two piece hard gelatin capsule shells.

[1]The amount of stearic acid may vary from 0.1% to 5.0% of the weight.
[2]The amount of water may vary to produce an acceptable granulation, and is dried off.
[3]The total fill weight (theoretical) does not include the residual moisture that will be present in the finished product.

Quantitative Composition of Ganciclovir Monoester Capsules
(Two Capsules Three Times Per Day)

| Ingredients | Weight Per Capsule (mg) | % W/W |
|---|---|---|
| Ganciclovir monoester hydrochloride | 312.00 | 92.75 |
| Povidone | 10.09 | 3.00 |
| Corn starch | 13.45 | 4.00 |
| Stearic acid[1] | 0.84 | 0.25 |
| Water[2] | | |
| Total fill weight (theoretical)[3] | 336.38 | 100.00 |

The powder blend is filled into two piece hard gelatin capsule shells.

[1]The amount of stearic acid may vary from 0.1% to 5.0% of the weight.
[2]The amount of water may vary to produce an acceptable granulation, and is dried off.
[3]The total fill weight (theoretical) does not include the residual moisture that will be present in the finished product.

Example of the Manufacturing Procedure for Ganciclovir Monoester Capsules

1. Blend the ganciclovir monoester and part of the corn starch in a suitable mixer.
2. Dissolve the povidone in the water with stirring.
3. Add (2) to (1) while continuing to mix to form a granulation.
4. Mill the wet granulation if necessary.
5. Dry the wet granulation in a dryer.

6. Pass the dry granulation, the remaining corn starch, and the stearic acid through mill.
7. Blend (6) in a suitable mixer.
8. Encapsulate the appropriate amount of (7) into 2 piece hard gelatin capsule shells.

What is claimed is:

1. A compound of the formula

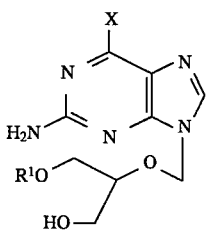

wherein:
X is hydrogen, chloro, amino or hydroxy; and
$R^1$ has the formula

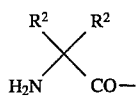

wherein:
each $R^2$ is alkyl with 2 to 6 carbon atoms, cycloalkyl with 3 to 5 carbon atoms, or benzyl; or the two $R^2$ group linked together form a polymethylene group with 3 to 9 carbon atoms;
or a pharmaceutically acceptable salt thereof.

2. A compound of the formula

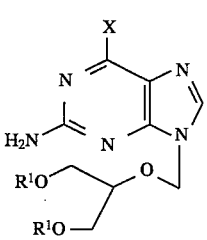

wherein:
$R^1$ has the formula

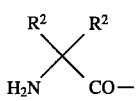

wherein:
each $R^2$ is alkyl with 2 to 6 carbon atoms, cycloalkyl with 3 to 5 carbon atoms, or benzyl; or the two $R^2$ group linked together form a polymethylene group with 3 to 9 carbon atoms;
or a salt thereof.

3. A compound according to claim 1 wherein:
$R^2$ is ethyl, propyl, butyl, cycloalkyl with 3 to 5 carbon atoms; or the two $R^2$ groups linked together form a polymethylene group with 3 to 9 carbon atoms;
or a pharmaceutically acceptable salt thereof.

4. A compound according to claim 3 wherein:
the two $R^2$ groups linked together form a polymethylene group with 3 to 9 carbon atoms;
or a pharmaceutically acceptable salt thereof.

5. A compound according to claim 4 wherein:
X is hydroxy.

6. A compound according to claim 5 wherein:
the two $R^2$ groups linked together form a polymethylene group with 4 or 5 carbon atoms;
or a pharmaceutically acceptable salt thereof.

7. A compound according to claim 6 or a pharmaceutically acceptable salt thereof wherein:
the two $R^2$ groups linked together form the group —$(CH_2)_5$—, that is 2-(2-amino-1,6-dihydro-6-oxo-purin-9-yl)methoxy-3-hydroxy-1-propanyl (1-amino-cyclohexane-carboxylate and its pharmaceutically acceptable salts.

8. A compound according to claim 6 or a pharmaceutically acceptable salt thereof wherein:
the two $R^2$ groups linked together form the group —$(CH_2)_4$—, that is 2-(2-amino-1,6-dihydro-6-oxo-purin-9-yl)methoxy-3-hydroxy-1-propanyl (1-amino-cyclopentane-carboxylate) and its pharmaceutically acceptable salts.

9. A compound according to claim 5 or a pharmaceutically acceptable salt thereof wherein:
the two $R^2$ groups linked together form the group —$(CH_2)_3$—, that is 2-(2-amino-1,6-dihydro-6-oxo-purin-9-yl)methoxy-3-hydroxy-1-propanyl (1-amino-cyclobutane-carboxylate) and its pharmaceutically acceptable salts.

10. The compound of claim 2 wherein:
X is hydroxy and the two $R^2$ groups are ethyl, that is 2-(2-amino-1,6-dihydro-6-oxo-purin-9-yl)methoxy-1,3-propanediyl bis(2-amino-2-ethylbutyrate) and its salts.

11. A compound according to claim 3 or a pharmaceutically acceptable salt thereof wherein:
the two $R^2$ groups are ethyl, that is 2-(2-amino-1,6-dihydro-6-oxo-purin-9-yl)methoxy-3-hydroxy-1-propanyl (2-amino-2-ethylbutyrate) and its pharmaceutically acceptable salts.

12. A compound according to claim 3 or a pharmaceutically acceptable salt thereof wherein:
the two $R^2$ groups are isopropyl, that is 2-(2-amino-1,6-dihydro-6-oxo-purin-9-yl)methoxy-3-hydroxy-1-propanyl (2-amino-2-isopropyl-3-methylbutyrate) and its pharmaceutically acceptable salts.

13. A compound according to claim 3 or a pharmaceutically acceptable salt thereof wherein:
the two $R^2$ groups are isobutyl, that is 2-(2-amino-1,6-dihydro-6-oxo-purin-9-yl)methoxy-3-hydroxy-1-propanyl (2-amino-2-isobutyl-3-methylvalerate) and its pharmaceutically acceptable salts.

14. A compound according to claim 3 or a pharmaceutically acceptable salt thereof wherein:
the two $R^2$ groups are n-butyl, that is 2-(2-amino-1,6-dihydro-6-oxo-purin-9-yl)methoxy-3-hydroxy-1-propanyl (2-amino-2-n-butylhexanoate) and its pharmaceutically acceptable salts.

15. A pharmaceutical composition comprising a compound according to claim 1 and a pharmaceutically acceptable excipient or carrier.

16. The compound of claim 2 wherein:
X is hydroxy and the two $R^2$ groups are n-propyl, that is 2-(2-amino-1,6-dihydro-6-oxo-purin-9-yl)methoxy-1,3-propanediyl bis (2-amino-2-n-propylvalerate) and its salts.

17. The pharmaceutical composition according to claim 15 adapted for intravenous administration.

18. A method of treating an animal afflicted with a herpes viral infection which method comprises administering a therapeutically effective amount of a compound of claim 1.

19. The method of claim 18 wherein the compound is administered orally.

20. The method of claim 18 wherein the compound is administered as a topical solution.

21. The method of claim 18 wherein the compound is administered as an intravitreal implant.

22. The compound of claim 2 wherein:

X is hydroxy and the two R² groups linked together form the group —(CH₂)₃—, that is 2-(2-amino-1,6-dihydro-6-oxo-purin-9-yl)methoxy-1,3-propanediyl bis (1-aminocyclo-butanecarboxylate) and its salts.

23. A compound of the formula

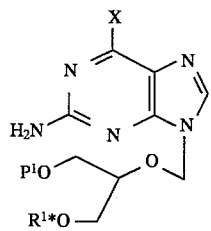

wherein:

X is hydrogen, chloro or hydroxy;

P¹ is a hydroxy-protecting group and R¹* is

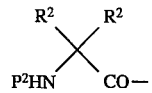

wherein:

each R² is alkyl with 2 to 6 carbon atoms, cycloalkyl with 3 to 5 carbon atoms, or benzyl; or the two R² group linked together form a polymethylene group with 3 to 9 carbon atoms; and P² is an amino-protecting group.

24. The compound of claim 2 wherein:

X is hydroxy and the two R² groups linked together form the group —(CH₂)₄—, that is 2-(2-amino-1,6-dihydro-6-oxo-purin-9-yl)methoxy-1,3-propanediyl bis (1-amino-cyclopentanecarboxylate) and its salts.

25. The compound of claim 2 wherein:

X is hydroxy and the two R² groups linked together form the group —(CH₂)₅—, that is 2-(2-amino-1,6-dihydro-6-oxo-purin-9-yl)methoxy-1,3-propanediyl bis (1-amino-cyclohexanecarboxylate) and its salts.

* * * * *

UNITED STATES PATENT AND TRADEMARK OFFICE
CERTIFICATE OF CORRECTION

PATENT NO. : 5,543,414
DATED : August 6, 1996
INVENTOR(S) : John J. Nestor et al.

It is certified that error appears in the above-indentified patent and that said Letters Patent is hereby corrected as shown below:

Claim 1, at column 35, line 29 "group" should read --groups--.

Claim 2, column 35, lines 43-44
"Wherein:
    $R^1$ has the formula" should read --Wherein:
    X is hydrogen, chloro, amino or hydroxy; and
    $R^1$ has the formula--.

and at column 35, line 54 "group" should read --groups--.

Claim 23, column 38, line 2 "X is hydrogen, chloro or hydroxy;" should read --X is hydrogen, chloro, amino or hydroxy;--.

and at column 38, line 12 "group" should read --groups--.

Signed and Sealed this

Fourteenth Day of January, 1997

Attest:

BRUCE LEHMAN

*Attesting Officer*          *Commissioner of Patents and Trademarks*